(12) United States Patent
Picardal et al.

(10) Patent No.: US 6,537,797 B1
(45) Date of Patent: Mar. 25, 2003

(54) COMPOSITIONS AND METHODS USEFUL IN BIOREMEDIATION OF POLYCHLORINATED BIPHENYLS

(75) Inventors: Flynn W. Picardal, Bloomington, IN (US); Sanggoo Kim, Bloomington, IN (US)

(73) Assignee: Indiana University, Advanced Research and Technology Institute, Indianapolis, IN (US)

( * ) Notice: Subject to any disclaimer, the term of this patent is extended or adjusted under 35 U.S.C. 154(b) by 0 days.

(21) Appl. No.: 09/539,606

(22) Filed: Mar. 31, 2000

Related U.S. Application Data

(60) Provisional application No. 60/127,214, filed on Mar. 31, 1999.

(51) Int. Cl.$^7$ ................................. B09B 3/00
(52) U.S. Cl. .................... 435/262.5; 435/243; 435/248; 435/252.1; 435/252.3; 435/253.3; 435/262; 435/262.5; 588/205; 588/207
(58) Field of Search ................................ 435/243, 248, 435/252.1, 252.3, 253.3, 262, 262.5; 588/205, 207

(56) References Cited

PUBLICATIONS

Novotny et al. Removal of PCBs by various white rot fungi in liquid cultures. Folia Microbiol (Praha) 1997;42(2):136–40.*

McCullar et al. Construction of a novel polychlorinated biphenyl–degrading bacterium: utilization of 3,4'–dichlorobiphenyl by *Pseudomonas acidovorans* M3GY. Appl. Environ Microbiol. 1994, vol. 60(10), pp. 3833–3839.*

Brenner et al., 1994, Biodegradation, 5:359–377.
Jeenes et al., 1982, J. Bacteriol. 150:180–187.
Kong and Sayler, 1983, Appl. Environ. Microbiol., 46:666–672.
Masse et al., 1984, Appl. Environ. Microbiol. 47:947–951.
McCullar et al., 1994, Applied and Environ. Microbiol. 60:3833–3839.
Shiaris and Sayler, 1982, Environ. Sci. Technol. 16:367–369.
Shields et al., 1985, J. of Bacteriol., 163:882–889.
Yagi and Sudo, 1980, J. Water Pollut. Control Fed. 52:1035–1043.

* cited by examiner

*Primary Examiner*—Nashaat T. Nashed
*Assistant Examiner*—Christian L. Fronda
(74) *Attorney, Agent, or Firm*—Morgan, Lewis & Bockius, LLP

(57) ABSTRACT

The invention includes an isolated bacterium and a consortium of microorganisms including an isolated bacterium of the invention, which is capable of utilizing as a sole carbon source a polychlorinated biphenyl. The invention also includes a recombinant microorganism, such as a bacterium, a yeast or a bacteriophage, transfected with nucleic acid from an isolated bacterium of the invention, which is capable of utilizing as a sole carbon source a polychlorinated biphenyl. The invention also includes an isolated bacterium, which is capable of utilizing as a sole carbon source a chlorobenzoate. In addition, the invention includes an isolated nucleic acid and recombinant enzymes useful in the degradation of a polychlorinated biphenyl. The invention also includes methods for the bioremediation or enhancement of the bioremediation of a PCB-contaminated environment using the bacteria or microorganisms of the invention.

25 Claims, 15 Drawing Sheets

COMPOSITIONS AND METHODS USEFUL IN BIOREMEDIATION OF POLYCHLORINATED BIPHENYLS

CROSS-REFERENCE TO RELATED APPLICATIONS

This application is entitled to priority pursuant to 35 U.S.C. §119(e) to U.S. provisional patent application 60/127,214, which was filed on Mar. 31, 1999.

STATEMENT REGARDING FEDERALLY SUPPORTED RESEARCH AND DEVELOPMENT

This invention was supported in part by U.S. Government funds (National Science Foundation grant number 9528939), and the U.S. Government may therefore have certain rights in the invention.

BACKGROUND OF THE INVENTION

Polychlorinated biphenyls (PCBs) represent a highly problematic environmental pollutant. They are ubiquitous in nature due to their widespread use as electrical insulators, and because of their unreactive chemical structure and low water solubility, they are generally considered to be nondegradable (Kalmaz et al., 1979, Review. Ecol. Model 6:223–251). PCB-contaminated waste is thus a major component of many environmentally-hazardous sites in need of remediation.

There have been several reports of PCB degradation and partial degradation by mixed (Clark et al., 1979, Appl. Environ. Microbiol. 37:680–685; Furukawa et al., 1978, Appl. Environ. Microbiol. 35:223–227; Huntzinger et al., ed., 1974. In: The chemistry of PCBs, p. 1–16, CRC Press, Inc., Boca Raton, Fla.; Kong and Sayler, 1983, Appl. Environ. Microbiol., 46:666–672; Shiaris and Sayler, 1982, Environ. Sci. Technol. 16:367–369) and pure (Ahmed and Focht, 1973, Can. J. Microbiol., 19:45–52; Jeenes et al., 1982, J. Bacteriol. 150:180–187; Mass et al., 1984, Appl. Environ. Microbiol. 47:947–951; Sayler et al., 1977, Microbial Ecology 3:241–255; Yagi and Sudo, 1980, J. Water Pollut. Control Fed. 52:1035–1043) bacterial cultures. Plasmid mediated degradation of mono-chlorobiphenyls has also been reported (Shields et al., 1985, J. of Bacteriol., 163:882–889). Both anaerobic and aerobic microorganisms capable of partially degrading or degrading certain types of PCBs under certain limited conditions have been reported. The reports include a recombinant bacterium capable of growth on a polychlorinated biphenyl as a sole carbon source (McCullar et al., 1994, Applied and Environ. Microbiol. 60:3833–3839). There have also been reports of consortia or mixed cultures of microorganisms which together are able to degrade PCBs (Brenner et al., 1994, Biodegradation, 5:359–377). Also, there have been reports of microorganisms capable of degrading PCBs when a cosubstrate, such as biphenyl or napthalene is added to the media to serve as a primary carbon source (see Brenner et al., 1994, Biodegradation, 5:359–377).

The aforementioned microorganisms are of limited usefulness and are inefficient in bioremediation methods because they either require the addition of a cosubstrate such as biphenyl or naphthalene, to enable the cometabolism of PCBs, or they are only capable of partially degrading PCBs to PCBs having fewer chlorine atoms or to other chlorinated aromatic molecules which cannot be further metabolized by living organisms. Although cosubstrates are potentially available to assist currently known microorganisms in the degradation of PCBs, typical cosubstrates are organic molecules which are themselves environmentally toxic, such as biphenyl and napthalene.

Thus, there is an unmet need for microorganisms that can be used in efficient and non-polluting bioremediation methods for PCB contaminated sites. It is especially desirable to have a bioremediation method of environmental cleanup that does not require the addition of another pollutant or chemical to the environment, and which utilizes readily available microorganisms. The present invention meets these needs.

BRIEF SUMMARY OF THE INVENTION

The invention includes an isolated bacterium, which is capable of utilizing as a sole carbon source a polychlorinated biphenyl, wherein the polychlorinated biphenyl contains at least two chlorine atoms associated therewith.

In one aspect, the polychlorinated biphenyl is 2,3-dichloro-biphenyl.

In another aspect, the polychlorinated biphenyl is 3,4-dichloro-biphenyl.

In yet another aspect, the polychlorinated biphenyl is 2,2'-dichloro-biphenyl.

In another aspect, the polychlorinated biphenyl is 2,4'-dichloro-biphenyl.

In one embodiment, the bacterium is strain SK-1.

In another embodiment, the bacterium is strain SK-2.

In another embodiment, the bacterium is strain SK-3.

In yet another embodiment, the bacterium is strain SK-4.

The invention also includes an isolated bacterium which is capable of utilizing as a sole carbon source a monochloro-biphenyl.

In one aspect, the monochloro-biphenyl is selected from the group consisting of 2-chlorobiphenyl, 3-chlorobiphenyl and 4-chlorobiphenyl.

In another aspect, the bacterium is strain SK-3.

The invention also includes an isolated bacterium which is capable of utilizing as a sole carbon source 4-chlorobenzoate.

Additionally, the invention includes an isolated bacterium which is capable of utilizing both 4-chlorobenzoate and a mono-chlorobiphenyl, individually, as a sole carbon source.

The invention also includes a consortium of microorganisms comprising a bacterium selected from the group consisting of SK-1, SK-2, SK-3 and SK-4.

The invention further includes a recombinant bacterium, which is capable of utilizing as a sole carbon source a polychlorinated biphenyl, wherein the polychlorinated biphenyl contains at least two chlorine atoms associated therewith.

Also included in the invention is a recombinant yeast, which is capable of utilizing as a sole carbon source a polychlorinated biphenyl, wherein the polychlorinated biphenyl contains at least two chlorine atoms associated therewith.

In addition, the invention includes a recombinant bacteriophage, comprising nucleic acid which when expressed in a bacterium infected with the bacteriophage confers on the bacterium the ability to utilize as a sole carbon source a polychlorinated biphenyl, wherein the polychlorinated biphenyl contains at least two chlorine atoms associated therewith.

The invention includes an isolated nucleic acid encoding an enzyme for degrading a polychlorinated biphenyl, wherein the nucleic acid is obtained from an isolated bacterium which is capable of utilizing as a sole carbon source a polychlorinated biphenyl, wherein the polychlorinated biphenyl contains at least two chlorine atoms associated therewith.

The invention also includes a recombinant enzyme for degrading a polychlorinated biphenyl wherein the recombinant enzyme is obtained from an isolated bacterium which is capable of utilizing as a sole carbon source a polychlorinated biphenyl, wherein the polychlorinated biphenyl contains at least two chlorine atoms associated therewith.

In one aspect, the recombinant enzyme is expressed in a bacterium.

In another aspect, the recombinant enzyme is expressed in a yeast.

In yet another aspect, the recombinant enzyme is substantially pure.

The invention also includes a method for the bioremediation of a PCB-contaminated environment. The method comprises the steps of a) adding an isolated bacterium to the PCB-contaminated environment, wherein the bacterium is capable of utilizing as a sole carbon source a polychlorinated biphenyl, wherein the polychlorinated biphenyl contains at least two chlorine atoms associated therewith, and b) incubating the bacterium in the environment for a period of time sufficient to permit degradation of a polychlorinated biphenyl in the environment, thereby bioremediating the environment.

Also included in the invention is a method for enhancing the bioremediation of a PCB-contaminated environment. The method comprises the steps of a) adding an isolated bacterium to the PCB-contaminated environment, wherein the bacterium is capable of utilizing as a sole carbon source a polychlorinated biphenyl, wherein the polychlorinated biphenyl contains at least two chlorine atoms associated therewith, and b) incubating the bacterium in the environment for a period of time sufficient to permit degradation of a polychlorinated biphenyl in the environment, thereby enhancing the bioremediation of the environment.

The invention further includes a method for the bioremediation of a PCB-contaminated environment. The method comprises the steps of a) adding an isolated bacterium to the PCB-contaminated environment, wherein the bacterium is capable of utilizing as a sole carbon source a polychlorinated biphenyl, wherein the polychlorinated biphenyl contains at least two chlorine atoms associated therewith; b) adding a cosubstrate selected from the group consisting of biphenyl and napthalene to the PCB-contaminated environment whereby cometabolism of the cosubstrate and a PCB may occur, and c) incubating the bacterium in the environment for a period of time sufficient to permit degradation of a polychlorinated biphenyl in the environment, thereby bioremediating the environment.

The invention also includes a method for the bioremediation of a PCB-contaminated environment. The method comprises the steps of a) adding a recombinant enzyme for degrading a polychlorinated biphenyl to the PCB-contaminated environment, wherein the recombinant enzyme is obtained from an isolated bacterium which is capable of utilizing as a sole carbon source a polychlorinated biphenyl, wherein the polychlorinated biphenyl contains at least two chlorine atoms associated therewith, and b) incubating the recombinant enzyme in the PCB-contaminated environment for a period of time sufficient to permit degradation of a polychlorinated biphenyl, thereby bioremediating the environment.

Additionally, the invention includes a method for the bioremediation of PCB-contaminated environment. The method comprises the steps of a) adding to the PCB-contaminated environment, a recombinant microorganism selected from the group consisting of a bacterium, a yeast, and a bacteriophage, wherein the recombinant microorganism comprises a nucleic acid encoding an enzyme for degrading a polychlorinated biphenyl, wherein the nucleic acid is obtained from an isolated bacterium which is capable of utilizing as a sole carbon source a polychlorinated biphenyl, wherein the polychlorinated biphenyl contains at least two chlorine atoms associated therewith, and b) incubating the recombinant microorganism in the PCB-contaminated environment for a period of time sufficient to permit degradation of a polychlorinated biphenyl, thereby bioremediating the environment.

The invention also includes a method for the bioremediation of a PCB-contaminated environment. The method comprises the steps of a) adding an isolated bacterium to the PCB-contaminated environment, wherein the bacterium is capable of utilizing as a sole carbon source a polychlorinated biphenyl, wherein the polychlorinated biphenyl contains at least two chlorine atoms associated therewith; b) adding an isolated bacterium to the PCB-contaminated environment, wherein the bacterium is capable of utilizing a chlorobenzoate as a sole carbon source, and c) incubating the bacteria in the environment for a period of time sufficient to permit degradation of a polychlorinated biphenyl and a chlorobenzoate in the environment, thereby bioremediating the environment.

BRIEF DESCRIPTION OF THE DRAWINGS

The foregoing summary, as well as the following detailed description of the invention, will be better understood when read in conjunction with the appended drawings.

FIG. 12, comprising

FIG. 13, comprising

FIG. 15, comprising FIG. 15A depicts cell numbers of washed, benzoate-grown SK-4 cells before and after incubation with Aroclor® 1242 (+PCB) and without Aroclor® 1242 (no PCB) as determined using the acridine orange direct counting method described herein. FIG. 15B is an image depicting a comparison of chromatograms obtained from gas chromatography analysis of a sample of Aroclor® 1242 which was not incubated with SK-4 (open bars) and a sample of Aroclor® 1242 which was incubated with SK-4 (closed bars). Peak heights of individual PCB congeners are shown for the comparison, and homologous groups of congeners (diCB, triCB, tetraCB, and pentaCB, where CB=chlorobiphenyl) were grouped as indicated according to retention times.

DETAILED DESCRIPTION

Figure 1:
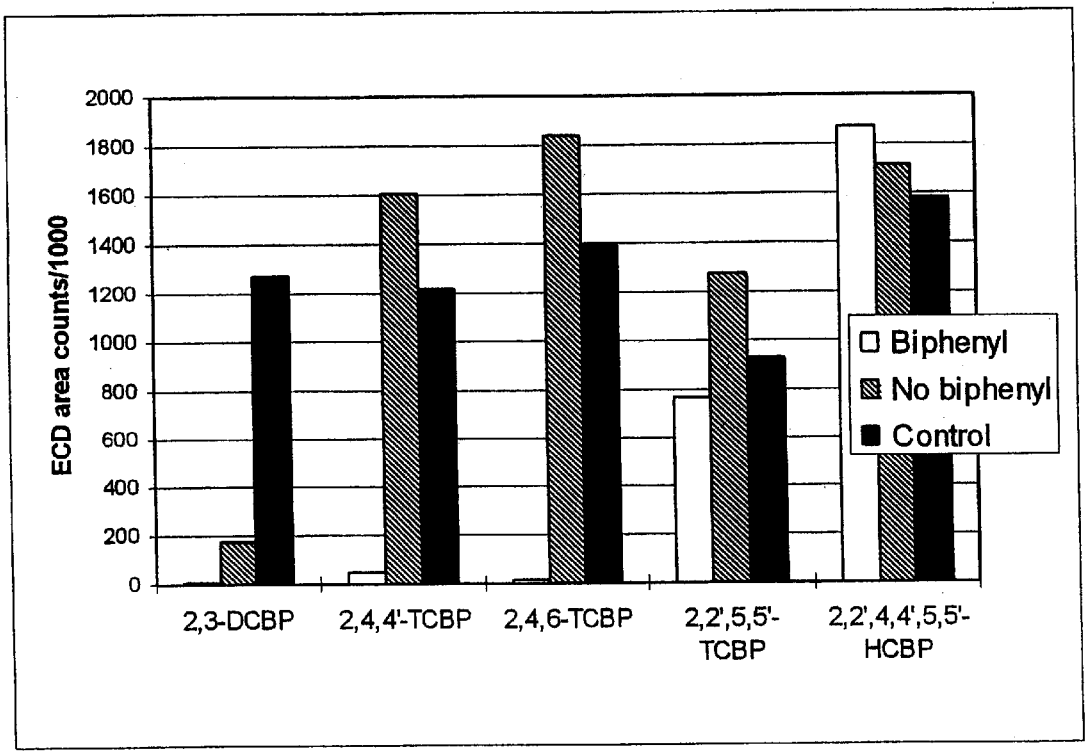
FIG. 1 is a graph depicting the degradation of selected PCB congeners in aerobic enrichment cultures. Results of control cultures lacking inoculum are shown in black bars. Results of cultures containing biphenyl as a primary carbon source are shown in open bars. Results of cultures containing selected congeners without the cosubstrate biphenyl are shown in striped bars. The concentrations of PCB congeners are expressed as gas chromatography peak area counts.

The present invention relates to novel methods and compositions useful for bioremediation of PCB contaminated wastes. The invention includes isolated bacteria capable of growth on a dichloro-biphenyl as a sole carbon source. The isolated bacteria of the invention and inventive methods using these bacteria are thus advantageous over conventional methods for bioremediation of PCB contaminated wastes.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, the term "polychlorinated biphenyl" (PCB) means a biphenyl molecule comprising a total of at least two chlorine atoms on the phenyl ring moieties of the molecule.

As used herein, the term "dichloro-biphenyl" means a polychlorinated biphenyl molecule having a total of two chlorine atoms on the phenyl ring moieties of the molecule, wherein the two atoms may be on the same or on different phenyl ring moieties.

As used herein, the term "monochloro-biphenyl" means a chlorinated biphenyl molecule having only one chlorine atom on a phenyl ring moiety of the molecule. The chlorine atom may be on either phenyl ring moiety.

As used herein, the term "congener" means an isomer of a polychlorinated biphenyl having a given number of total chlorine atoms on the biphenyl ring moieties.

As used herein, the term "isolated bacterium" means a naturally occurring bacterium that has been physically isolated and separated from the components with which it is naturally associated. For example, a bacterium may be physically isolated from sludge or soil where it was found, and from a culture of another microorganism, such as a different bacterial species.

As used herein, the term "degrades" or "degrading" means to metabolically breakdown a chemical compound, such as a PCB, to a less complex molecule. The chemical compound may or may not be utilizable as a carbon source in metabolism by a microorganism, or may or may not be utilizable as a sole carbon source for growth of a microorganism. For example, a PCB may be degraded to a chlorinated pentadiene and a chlorobenzoate molecule, and either one may be used as a carbon source for growth of a microorganism.

As used herein, the term "cosubstrate" means a primary carbon or energy source, which is added to stimulate the degradation or metabolism of a PCB or other molecule.

As used herein, the term "bioremediation" means a treatment method for an environmentally contaminated waste to render such waste less toxic to the environment than before treatment began, or to render the waste susceptible to metabolism by a microorganism or group of microorganisms, wherein the method includes the application of a living organism or a product produced thereby as a component of the treatment process.

As used herein, the term "recombinant bacterium" means a host bacterium that comprises a recombinant polynucleotide, which is a polynucleotide having sequences that are not naturally joined together. An amplified or assembled recombinant polynucleotide may be included in a suitable vector, and the vector can be used to transform a suitable host cell. A recombinant polynucleotide may serve a non-coding function (e.g., promoter, origin of replication, ribosome-binding site, etc.) as well.

As used herein, the term "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

As used herein, the term "operably linked" means that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, the term "recombinant enzyme" means an enzyme which is produced upon expression of a recombinant polynucleotide.

Description

The invention relates to isolated bacteria which are capable of growth on a PCB as a sole carbon source, without the aid of a toxic cosubstrate, or the aid of another recombinant or naturally occurring microorganism. The isolated bacteria of the invention are ideally suited to assist in effective and safe methods for bioremediation of PCB contaminated waste sites.

The invention includes an isolated bacterium, which is capable of utilizing, as a sole carbon source, a polychlorinated biphenyl (PCB), containing at least two chlorine atoms. The bacterium of the invention may be isolated by any isolation method known to those skilled in the art. For example, the bacterium may be isolated from an environmental sample of soil, sludge, sediment, or water, which has been contaminated with PCBs for a long period of time.

The bacterium of the invention may be isolated and enriched by any enrichment method that favors the growth of PCB-degrading bacteria over that of other microorganisms. For example, a selected congener may be used as a carbon source or a sole carbon source in a growth medium for enrichment of PCB-degrading bacteria from an environmental sample. Once the PCB degrading bacteria are the numerically dominant species in the enrichment culture, the PCB-degrading bacteria can be isolated using a number of different methods, such as plating the bacteria on selective media or serial dilution of the bacteria in selective media.

A preferred method for isolating the bacterium of the invention is by obtaining a sample such as a soil or sediment sample, which is contaminated by PCBs, and incubating the sample with a minimal medium which contains one or more PCBs as the carbon source. One example of a preferred minimal medium contains, per liter, 0.5 grams of ammonium sulfate, 0.1 grams of magnesium sulfate heptahydrate, and 0.076 grams of calcium nitrate in a 40 millimolar, pH 7.2 phosphate buffer. Trace metal and vitamin solutions may also be added. The concentration of PCBs added to the minimal medium should provide a sufficient amount of carbon and energy to allow for enrichment of the bacteria, but should not be toxic to the bacteria. This range may be estimated as between about 0.5 ppm to about 10,000 ppm. An example of a preferred PCB concentration is 100 parts per million (w/v).

Optionally, a cosubstrate such as biphenyl, may also be added to the minimal medium as an additional carbon source to stimulate the cometabolism of the PCBs. The PCBs added to the minimal medium can be added as a combination of PCBs, or as a single PCB congener.

The medium can then be inoculated with the PCB contaminated sample and incubated in a suitable vessel such as a bottle. Cultures can be grown in the vessel for a period of time, for example, about 4–6 weeks, although incubation periods which are as short as three days or as long as three months may be used. Following incubation, a fraction of the culture can be transferred to fresh medium containing PCB congeners. A number of transfers, ranging from about 3 to about 20, can be performed to result in an enriched culture of an isolated bacterium which is capable of growth on PCBs. A preferred number of transfers is about 10 transfers.

The isolated bacterium of the invention is exemplified by four isolated strains of bacteria, strains SK-1, SK-2, SK-3, and SK-4, which are all capable of degrading a PCB congener. These four isolated bacterial strains are capable of growth on a polychlorinated biphenyl as a sole carbon source. One of the bacterial strains, SK-3, is capable of growth on both a polychlorinated biphenyl and a chlorobenzoate, individually, as a sole carbon source. For example, strain SK-3 produces no chlorobenzoates when grown on 4-mono-chlorobiphenyl as a sole carbon source. This is a result of the unique ability of SK-3 to grow on both 4-monochlorobiphenyl, and its degradation product, 4-chlorobenzoate, individually, as a sole carbon source. The preferred polychlorinated biphenyl for SK-1 is 2,3-dichloro-biphenyl; for SK-2 is 3,4-dichloro-biphenyl; for SK-3 is 2,4'-dichloro-biphenyl and for SK-4 is 2,2'-dichloro-biphenyl and 2,4'-dichloro-biphenyl. However, the invention should not be construed to be limited solely to these isolated bacteria. Rather, the invention should be construed to include any and all PCB degrading bacteria which can be isolated according to the above-described method.

The invention includes PCB degrading bacteria which may be isolated from a PCB contaminated environment by using a method of isolation and enrichment as described herein. As used herein, the term "environment" includes sludges, sediments, soils and waters which may be found anywhere.

In one embodiment, the invention includes the individual bacterial strains SK-1, SK-2, SK-3, and SK-4, and in other embodiments, the invention includes any combination of these strains. For example, two of the strains, SK-1 and SK-2, may be used together in the bioremediation of PCB-contaminated waste.

In addition to including a combination of the above strains of bacteria, the invention also includes a consortium of microorganisms that comprises at least one of the bacterial strains described above. This consortium of microorganisms can include any microorganism that is useful in the bioremediation of PCB treated waste. Such microorganisms may include yeast, bacteria, fungi, plants, viruses, and other microorganisms. A more preferred microorganism is a microorganism capable of degrading or partially degrading a PCB either alone or in combination with another microorganism. A preferred microorganism is a bacterium, which may be either an isolated naturally occurring bacterium, or a recombinant bacterium.

The invention also includes a recombinant bacterium produced by transfecting a desired bacterium with nucleic acid obtained from the bacterium of the invention. A recombinant bacterium which is capable of bioremediation of PCBs as defined herein may be generated as follows. DNA is obtained from any of the isolated bacteria of the invention. The DNA is introduced into a desired bacterium using any of the well known bacterial DNA transfection procedures which are described, for example in Sambrook et al., 1989, Molecular Cloning: A Laboratory Manual, Cold Spring Harbor Laboratory, New York; Ausubel et al., 1994, Current Protocols in Molecular Biology, John Wiley & Sons, New York; and Gerhardt et al., eds., 1994, Methods for General__ and Molecular Bacteriology, American Society for Microbiology, Washington, D.C. Bacteria into which the DNA is introduced are tested for their ability to degrade PCBs as described herein, and those which are found to degrade PCBs are isolated.

To determine whether a recombinant bacterium is capable of degrading PCBs in a manner useful in the methods of the present invention, the recombinant bacterium (the test bacterium) is propagated on a medium which contains the appropriate PCBs and degradation of the PCBs by the bacterium is assessed. Such PCB degrading assays are provided herein in the Experimental Examples.

In one embodiment, the DNA which is obtained from the isolated bacterium of the invention is first fragmented into pieces using restriction enzymes or simply by physically shearing the DNA. The fragments of DNA so produced are then introduced into the desired bacterium, and these bacteria are then tested for the ability to degrade PCBs as described herein.

In another embodiment, a bacterial expression library of DNA obtained from the isolated bacterium of the invention is generated. The library may be made in a bacterial expression vector, which is any vector suitable for use in the transfer and expression of a nucleic acid into a bacterial cell, wherein, for example, each DNA fragment is cloned in a manner so as to be operably linked to a promoter/regulatory sequence which drives expression of the DNA fragment operably linked thereto. Such cloning methods are described, for example, in Sambrook et al., 1989, Molecular Cloning: A Laboratory Manual, Cold Spring Harbor Laboratory, New York; Ausubel et al., 1994, Current Protocols in Molecular Biology, John Wiley & Sons, New York; and Gerhardt et al., eds., 1994, Methods for General__and Molecular Bacteriology, American Society for Microbiology, Washington, D.C. A suitable bacteriophage is lambda bacteriophage, and a suitable host bacterium is *E. coli* for generating such libraries.

The recombinant bacterium may then be propagated in a medium containing a PCB or PCBs, wherein a detectable marker is employed, such as a color producing agent, or wherein an enzyme substrate is used to detect the degradation of the PCBs in the medium, or the growth of the recombinant bacterium on the medium. Bacteria which comprise DNA encoding PCB degrading enzymes degrade the PCB or PCBs and are therefore detectable using the marker. These bacteria can therefore be selected as the recombinant bacteria of the invention. Recombinant DNA contained therein may be isolated and further characterized for the ability to encode enzymes which degrade PCBs. Such genes and enzymes may then be isolated using ordinary molecular biology and biochemical technology which is well known in the art.

For example, in one embodiment, transfected bacteria can be propagated on a plate or on a filter with medium containing a cosubstrate such as biphenyl as a marker. Bacterial growth on a plate containing such a medium results in a zone of clearing as the biphenyl layer is consumed around the colonies. Selected colonies growing on biphenyl can then be transferred back to medium containing individual PCBs to confirm that the recombinant bacterium is capable of growth on PCBs as a sole carbon source.

The recombinant bacterium may be any bacterium susceptible to transfection by standard methods and procedures well known to those skilled in the art. The resulting recombinant bacterium is an organism that is able to utilize a polychlorinated biphenyl, such as a dichloro-biphenyl, as a sole carbon source. An example of a preferred recombinant bacterium is the bacterium E. coli.

The invention also includes a recombinant yeast cell produced by transfecting a desired yeast cell with nucleic acid of the bacterium of the invention. A recombinant yeast cell which is capable of bioremediation of PCBs as defined herein may be generated in substantially the same way as that described herein for the generation of a recombinant bacterium. Essentially, DNA is obtained from any of the isolated bacteria of the invention. The DNA is fragmented and introduced into a desired yeast cell as described herein. Yeast cells into which the DNA is introduced are tested for their ability to degrade PCBs as described herein, and those which are found to degrade PCBs are isolated.

In one embodiment, the DNA which is obtained from the isolated bacterium of the invention is first fragmented into pieces using restriction enzymes or simply by physically shearing the DNA. The fragments of DNA so produced are then introduced into the desired yeast cells, and these yeast cells are then tested for the ability to degrade PCBs as described herein.

In yet another embodiment, a yeast expression library of DNA obtained from the isolated bacterium of the invention is generated. The library may be made in a yeast expression vector, which is any vector suitable for use in the transfer and expression of a nucleic acid into a yeast cell, wherein, for example, each DNA fragment is cloned in a manner so as to be operably linked to a promoter/regulatory sequence which drives expression of the DNA fragment operably linked thereto.

The recombinant yeast cells may then be propagated in a medium containing a PCB or PCBs, wherein a detectable marker is employed, such as a color producing agent or an enzyme substrate, is used as described herein to detect the degradation of the PCBs in the medium or the growth of the recombinant yeast cells on the medium. Yeast cells which comprise DNA encoding PCB degrading enzymes will degrade the PCB or PCBs and be detectable by the marker, and can therefore be selected as the recombinant yeast cells of the invention.

The recombinant yeast cell may be any yeast cell that is susceptible to nucleic acid transfection by standard methods well known to those skilled in the art. After transfection, the resulting recombinant yeast cell is a yeast cell that is capable of utilizing a dichloro-biphenyl as a sole carbon source. An example of a preferred recombinant yeast cell is *Saccharomyces cerevisiae*.

The invention also includes a recombinant bacteriophage produced by transfecting a desired bacteriophage with fragmented nucleic acid of the bacterium of the invention as described herein. In one embodiment, a bacteriophage expression library of DNA obtained from the isolated bacterium of the invention is generated. The library may be made in a bacteriophage expression vector, which is any vector suitable for use in the transfer and expression of a nucleic acid into a bacteriophage, wherein, for example, each DNA fragment is cloned in a manner so as to be operably linked to a promoter/regulatory sequence which drives expression of the DNA fragment operably linked thereto. Such cloning methods are described, for example, in Sambrook et al., 1989, Molecular Cloning: A Laboratory Manual, Cold Spring Harbor Laboratory, New York; Ausubel et al., 1994, Current Protocols in Molecular Biology, John Wiley & Sons, New York; and Gerhardt et al., eds., 1994, Methods for General and Molecular Bacteriology, American Society for Microbiology, Washington, D.C.

Bacteriophage into which the fragments of DNA are introduced are used to infect bacteria for replication therein. The bacteriophage-infected bacteria may then be propagated in a medium containing a PCB or PCBs, wherein a detectable marker is employed as described above. Bacteria infected with bacteriophage comprising DNA encoding PCB degrading enzymes will degrade the PCB or PCBs and be detectable by the marker, and can therefore be selected. These bacteria comprise the recombinant bacteriophage of the invention. The recombinant bacteriophage of the invention can be used to transfect other bacteria and confer to an infected bacterium the ability to degrade PCBs. An example of a preferred recombinant bacteriophage is lambda bacteriophage.

The invention also includes an isolated nucleic acid, useful for transfecting a microorganism to confer on the microorganism the ability to degrade or partially degrade PCBs, such as dichlorobiphenyls. The isolated nucleic acid may be obtained by cloning a DNA obtained from an expression library of a bacterium of the invention. Methods of cloning and generating DNA expression libraries are well known to those skilled in the art and are described, for example, in Sambrook et al., 1989, Molecular Cloning: A Laboratory Manual, Cold Spring Harbor Laboratory, New York; Ausubel et al., 1994, Current Protocols in Molecular Biology, John Wiley & Sons, New York; and Gerhardt et al., eds., 1994, Methods for General and Molecular Bacteriology, American Society for Microbiology, Washington, D.C.

The isolated nucleic acid may also be obtained by cloning DNA from a recombinant bacterium of the invention using, for example, restriction enzymes and a bacterial cloning vector, such as a plasmid, and a bacterial expression system, such as E. coli. In another embodiment, the isolated nucleic acid may be obtained by cloning DNA from a recombinant bacteriophage of the invention using, for example, restriction enzymes, a viral vector, and a bacteriophage expression system. Also, the isolated nucleic acid may be obtained by cloning DNA from a recombinant yeast cell of the invention, using, for example, restriction enzymes, a yeast vector and a yeast expression system. The cloned nucleic acid may be isolated from the host microorganism by an amplification method, such as the polymerase chain reaction (PCR) followed by a nucleic acid purification method. Such methods are well known to those skilled in the art. The isolated nucleic acid may be used to transfect a microorganism as described herein, to confer the ability to degrade or partially degrade PCBs.

The invention also includes a recombinant enzyme for degrading or partially degrading a polychlorinated biphenyl, such as a dichloro biphenyl. Such an enzyme may be obtained from an isolated bacterium of the invention by cloning a cDNA obtained from an expression library of an isolated bacterium of the invention and screening for an enzyme exhibiting activity in degrading or partially degrading a polychlorinated biphenyl, such as a dichloro-biphenyl, in a PCB-contaminated sample. Assays for degradation of PCBs are provided in the Experimental Examples section herein.

The recombinant enzyme of the invention may also be obtained from a recombinant bacterium, a recombinant yeast cell, or a recombinant bacteriophage of the invention by cloning a DNA obtained from an expression library from the recombinant microorganism into an appropriate expression system and screening for an enzyme exhibiting activity in degrading or partially degrading a polychlorinated biphenyl, such as a dichloro-biphenyl, in a PCB-contaminated sample as described herein. An example of such a screening method is a method for detecting the production of chloride by the enzymatic degradation of PCBs by using a chloride ion-specific electrode.

The recombinant enzyme of the invention may be expressed in a microorganism that is suitable for the expression of a recombinant enzyme, such as the bacterium *E. coli*. The recombinant enzyme of the invention may also be expressed in a yeast. Suitable yeast expression systems for recombinant enzymes are well known to those skilled in the art.

In one embodiment, the invention includes a substantially pure recombinant enzyme as described above. The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state. Methods for the purification of recombinant enzymes are well known to those skilled in the art, and may include for example, liquid chromatography methods such as ion exchange, size exclusion and affinity chromatography, ammonium sulfate precipitation, and ultracentrifugation. The purity of the recombinant enzyme may be assessed by a method such as SDS-PAGE followed by Coomassie Blue or silver staining methods or immunological methods. These methods are well known to those skilled in the art and kits are commercially available to assess purity by SDS-PAGE.

The invention further includes a method for the bioremediation of a PCB-contaminated environment, used synonymously herein with the term "waste". Environments such as soils, sludges, sediments and waters which are contaminated by one or multiple PCB congeners are included in the invention. In one embodiment, the method of the invention comprises the addition of a culture of one of the isolated bacterial strains of the invention, preferably SK-1, SK-2, SK-3 or SK-4, to the PCB contaminated waste. The culture can then be incubated in the environment without any added cosubstrate, or other carbon or energy source. This is important because it results in a more efficient bioremediation method for two reasons. First, there is no need to add cosubstrates, which are themselves toxic molecules, to an already polluted PCB-contaminated environment. Second, because the isolated bacterium of the invention can grow on PCBs as a sole carbon source, they are capable of complete degradation, not just partial degradation, of PCBs. In the method of the invention, a sufficient time is allowed for the isolated bacterium of the invention to degrade the dichloro-biphenyls to metabolic intermediates.

For example, one of the isolated bacterial strains of the invention can be added to a PCB-contaminated environment at an initial inoculum of about 10,000 to about 100,000 cells per milliliter of sludge or soil. The bacterial strain of the invention is then incubated in the PCB-contaminated environment for a period ranging from about one to about twelve months to degrade the PCBs. A nitrogen and a phosphorus source at a concentration of about 1 millimolar each can also be added. The process of PCB degradation can be monitored by periodically taking samples of the PCB-contaminated environment and extracting the PCBs with hexane, and analyzing PCBs in the extract using a gas chromatography method. The degradation products may include chlorobenzoic acids, carbon dioxide, chloride ion, and other compounds depending on the extent of PCB degradation.

In one embodiment, the isolated bacterium of the invention can be added to a PCB-contaminated environment as described herein to enhance bioremediation in combination with other agents effective in the bioremediation of PCBs. These other agents may include a microorganism or more than one microorganism, such as a bacterium, a yeast, a fungus or plant. The agents may also include a chemical compound that is not lethal to the bacterial strain of the invention, but is effective at degrading or partially degrading PCBs. For example, Fenton's reagent, formed by mixing hydrogen peroxide and ferrous iron, is one chemical agent that can be used in bioremediation along with the isolated bacterium of the invention. The use of Fenton's reagent results in the generation of hydroxyl radicals which are very effective oxidizing agents. These hydroxyl radicals may partially cleave or hydroxylate the aromatic ring moieties of PCBs, rendering them more soluble and more amenable to attack by a microorganism.

When the other agent in bioremediation is a microorganism, the microorganism or microorganisms used may be an isolated naturally occurring microorganism, or may be a genetically engineered or recombinant microorganism. For example, the microorganism may be a bacterium capable of partial degradation of a PCB congener to a dichloro-biphenyl. The bacterial strain of the invention can then complete the degradation of the dichloro-biphenyl to metabolic intermediates which are non-toxic to living systems.

In another embodiment, a combination of more than one of the bacterial strains SK-1, SK-2, SK-3 and SK-4 may be used in a PCB bioremediation method as described above. The combination of strains of the invention may be used as the sole method of bioremediation, or as a method for enhancing the bioremediation of other agents effective at degrading or partially degrading PCBs.

In another embodiment of the method of the invention, one or more than one of the bacterial strains SK-1, SK-2, SK-3 and SK-4 is added to PCB-contaminated waste along with a cosubstrate to aid in the degradation of PCBs. The cosubstrate may be an organic molecule that is chemically similar to the non-halogenated nucleus of a PCB, such as biphenyl or napthalene, which is used as a carbon source to aid in the degradation of PCBs. The cosubstrate may be added, for example, at a concentration ranging from about 1 ppm to about 500 ppm. The isolated bacterium of the invention can be used with a cosubstrate as the sole agents of PCB bioremediation in one embodiment of the method of the invention.

In another embodiment of the invention, the method of the invention comprises the addition as described herein of a culture of an isolated bacterium of the invention capable of degrading a polychlorinated biphenyl, for example, SK-1, SK-2, SK-3 or SK-4, and the addition as described herein of a culture of an isolated bacterium of the invention capable of degrading a chlorobenzoate, for example SK-3, to a PCB-contaminated environment. The cultures can then be incubated in the environment as described herein with or without an added cosubstrate, or other carbon or energy source, to bioremediate and degrade PCBs in the environment. The use of both PCB degrading and chlorobenzoate degrading bacteria results in an effective bioremediation method.

In another embodiment of the invention, the isolated bacterium of the invention can be used with a cosubstrate to enhance PCB bioremediation along with another agent effective at degradation or partial degradation of PCBs. These other agents are as described herein, and may include a microorganism or more than one microorganism, such as bacteria, yeast, fungi or plant. These agents may also include a chemical compound that is not lethal to the bacterial strain of the invention, but is effective at degrading or partially degrading PCBs. The microorganism or microorganisms used may be an isolated naturally occurring microorganism, or may be a genetically engineered or recombinant microorganism. For example, the microorganism may be a recombinant E. coli bacterium capable of partial degradation of a PCB congener to a dichloro-biphenyl. The isolated bacterium of the invention can then complete the degradation of the dichloro-biphenyl to metabolic intermediates which are non-toxic to living systems.

The invention also includes a method for the bioremediation of PCB-contaminated wastes comprising adding a recombinant enzyme of the invention to PCB-contaminated soils, sludges, sediments and waters. A recombinant enzyme of the invention is an enzyme capable of degrading or partially degrading PCBs and is obtained from an isolated bacterium selected from the group consisting of SK-1, SK-2, SK-3 and SK-4 or any other bacterium encompassed by the invention. In the method of the invention, a recombinant enzyme of the invention is added to the PCB contaminated waste at a concentration in the range from about 1 picogram per milliliter to about 20 grams per milliliter, and the enzyme is incubated in the waste for a period of time sufficient to permit degradation or partial degradation of a PCB congener or more than one PCB congener. This time period may be, for example, from about several hours to about several years. The method may optionally include adding a cofactor or a metal ion, such as NADH/NAD+ or $Mg^{+2}$, to assist in the degradation catalyzed by the recombinant enzyme.

In one embodiment the recombinant enzyme is added to the waste as the sole agent in PCB bioremediation. In a preferred embodiment, the recombinant enzyme is substantially pure, as described herein.

In another embodiment the recombinant enzyme is added to the waste along with another agent effective at PCB degradation or partial degradation. The other agent may be a bacterial strain or strains of the invention selected from the group including SK-1, SK-2, SK-3 and SK-4. The other agent may also be another microorganism as described herein. In addition, the other agent may be a chemical agent as described herein.

The invention also includes a method for the bioremediation of PCB-contaminated wastes comprising adding a recombinant microorganism, or more than one recombinant microorganism of the invention to PCB-contaminated waste and incubating the recombinant microorganism in the waste for a period of time sufficient to degrade or partially degrade PCBs. The recombinant microorganism of the invention may be a bacterium, a yeast or a bacteriophage as described above herein, which has been transfected with a nucleic acid from a bacterial strain of the invention selected from SK-1, SK-2, SK-3 or SK-4.

The recombinant microorganism or microorganisms may be added to the waste as the sole agent in PCB bioremediation. In a preferred embodiment, the microorganism is a recombinant bacterium, capable of growth on a dichloro-biphenyl as a sole carbon source.

In another embodiment, the recombinant microorganism may be added to the waste along with another agent effective at PCB degradation or partial degradation. The other agent may be a bacterial strain or strains of the invention selected from the group including SK-1, SK-2, SK-3 and SK-4. The other agent may also be another microorganism as described above herein. In addition, the other agent may be a chemical agent as described above herein.

The invention is now described with reference to the following Examples. The Examples are provided for the purpose of illustration only, and the invention should in no way be construed as being limited to the Examples, but rather should be construed to encompass any and all variations which become evident as a result of the teaching provided herein.

EXAMPLE 1

Isolation and Characterization of an Isolated Bacterium Capable of Growth on a Dichloro-biphenyl The data presented in this Example provide procedures for the isolation of a consortia of bacterial strains, capable of degrading PCBs. Individual bacterial strains capable of growth on dichlorobiphenyl as a sole carbon source were isolated and enriched. These individual strains are valuable for use in bioremediation of PCB contaminated soils, sludges and waters either alone, in combination with other microorganisms in a consortia or in a mixed culture.

Isolation of PCB-degrading bacterial strains

A consortia of bacterial strains was isolated from tertiary lagoon sludge that was contaminated with PCBs for over twenty five years. The sludge was collected from the Winston-Thomas sewage treatment plant in Bloomington, Ind. PCB-degrading strains were enriched using a minimal medium comprising a 100 ppm (w/v) mixture of the following five PCB congeners as the carbon source: 2,3-dichlorobiphenyl (DCBP), 2,4,4'-trichlorobiphenyl (TCBP), 2,4,6-trichlorobiphenyl, 2,2',5,5'-tetrachlorobiphenyl, and 2,2',4,4',5,5'-hexachlorobiphenyl. Biphenyl was also added to the medium in some samples as an additional carbon source to stimulate the cometabolism of biphenyl and the PCBs. About 30–35 milliliters of the medium was inoculated with 5–10 milliliters of PCB-contaminated sludge and incubated in 160-mL serum bottles sealed with Teflon-coated stoppers. The bottles were incubated horizontally on a shaker table at room temperature. The headspace in the bottles was purged with air once a week to maintain aerobic conditions. Every 4–6 weeks, 10% of the culture was transferred to fresh medium. After seven such transfers, bottles which exhibited significant turbidity were analyzed to determine the concentrations of the 5 PCB congeners added with the fresh growth medium during each transfer. The concentrations of the PCB congeners were determined by extracting bottles with hexane 45 days after inoculation (a single bottle extraction), and analyzing hexane extracts by gas chromatography using a DB-5 column (J&W Scientific, Folsum, Calif.) and an electron capture detector. The results from this analysis are depicted in FIG. 1.

The two trichlorobiphenyls (2,4,4'- and 2,4,6-TCBP) were degraded only in the bottles which contained biphenyl as a cosubstrate, which are indicated by the open bars in FIG. 1.

2,3-dichlorobiphenyl (2,3-DCBP) was degraded in bottles which lacked a cometabolic substrate, as depicted by the striped bars. The data indicated that 2,3-dichlorobiphenyl was degraded in bottles which contained the dichlorobiphenyl 2,3-DCBP as the sole carbon and energy source and in bottles which contained biphenyl at a concentration of 100 milligrams per liter as a cosubstrate.

The results described above were obtained using bottles of microbial consortia rather than pure cultures. The consortia was transferred into a minimal medium which contained only a single congener, (e.g., 2,3-DCBP, 3,4-DCBP and 2,2'-DCBP) and the use of biphenyl as a cosubstrate was discontinued. After three transfers in liquid media containing individual congeners, portions of cultures were streaked on a minimal solid medium covered with a biphenyl layer. Bacteria growing on these plates exhibited a zone of clearing as the biphenyl layer was consumed around the colonies. Selected colonies growing on biphenyl were transferred back to the liquid medium containing individual congeners to confirm that they were capable of growth on PCBs as a sole carbon source. After three passages on solid medium containing biphenyl and liquid medium containing selected PCB congeners, the purity of isolates was confirmed by two passages on non-selective nutrient agar media.

Characterization and identification of bacterial strains

Cultures purified as described above were characterized using two different methods to match them with known microbial strains. Cultures were characterized using the API 20 E system (BioMerieux Vitek, Inc., Hazelwood, Mo.) for the identification of gram-negative bacteria. Cultures were also characterized by an analysis performed by Microbial I.D. (Newark, Del.) for identification using fatty acid profiles. Four different bacterial strains were isolated. These strains were named SK-1, SK-2, SK-3 and SK-4. Table 1 contains a list of the species having characteristics similar to the four isolated PCB-degrading strains. Further characterization of species identity is carried out using 16S ribosomal RNA sequence analysis.

The ability of the four isolated strains to grow on selected polychlorobiphenyls as a sole carbon source was assessed. The results from these experiments are shown in Table 2. These results may be summarized as follows: SK-1 exhibited growth on 2,3-DCBP as the sole carbon source; SK-2 exhibited growth on 3,4-DCBP as the sole carbon source; SK-3 exhibited growth on each of 2,4'-DCBP, 4-chlorobiphenyl, and 4-chlorobenzoate as the sole carbon source, and SK-4 exhibited growth on each of 2,2'-DCBP and 2,4'-DCBP as the sole carbon source. In addition to the ability to grow on the PCB congeners described above, all of the strains were able to grow on monochlorobiphenyls (e.g., 2-chlorobiphenyl, 3-chlorobiphenyl and 4-chlorobiphenyl).

Characterization of bacterial strains SK-1 and SK-2

Figure 2:
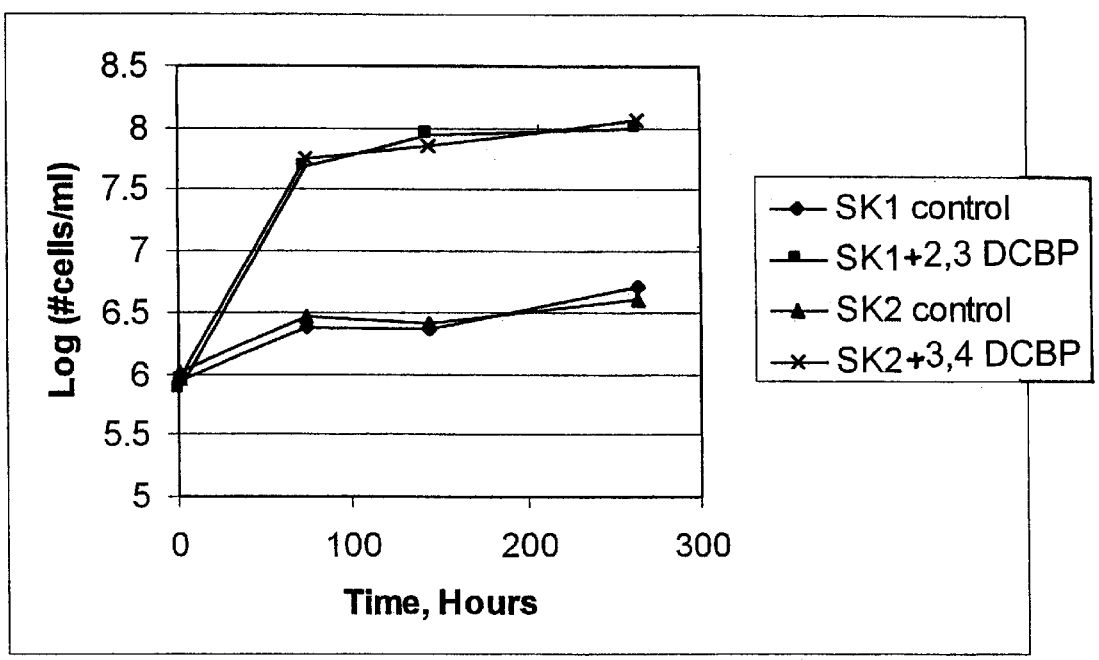
FIG. 2 is a graph depicting the growth of two isolated bacterial strains, SK-1 and SK-2, on 2,3-dichloro-biphenyl (2,3-DCBP) and 3,4-dichlorobiphenyl (3,4-DCBP), respectively. Controls are identical to experimental cultures, but lack the dichlorobiphenyl congener.
Figure 3:
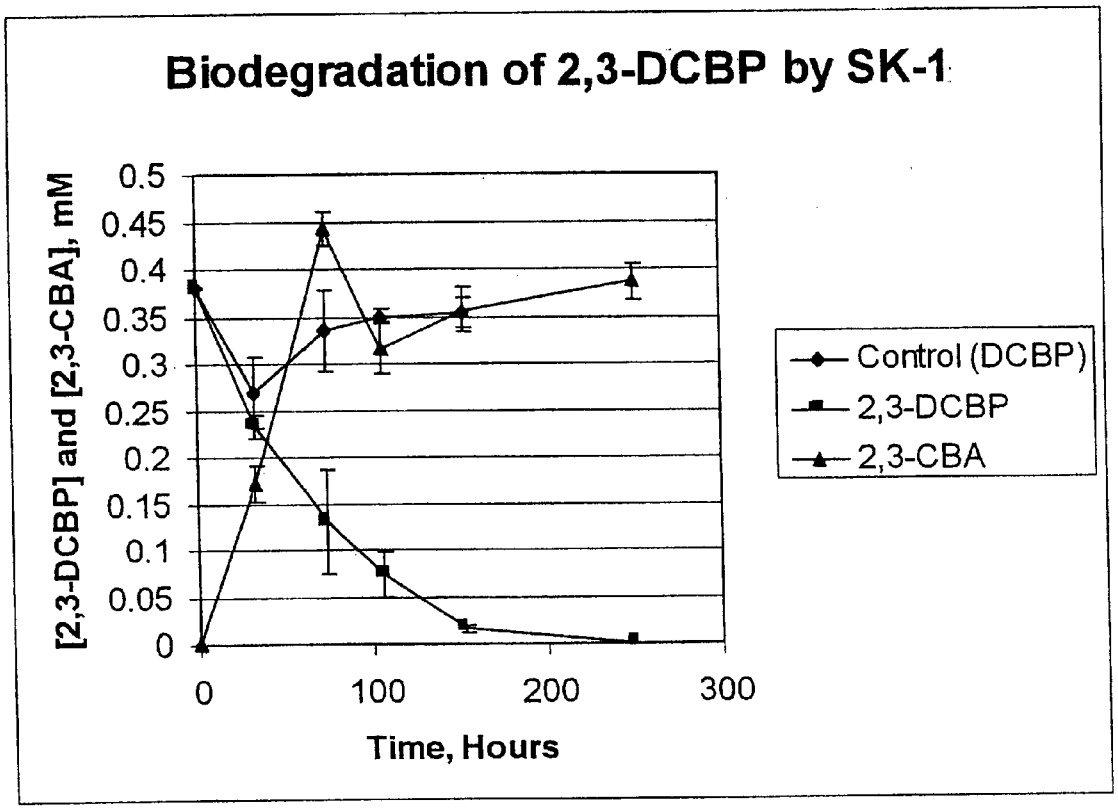
FIG. 3 is a graph depicting the degradation of 2,3-dichlorobiphenyl (2,3-DCBP) to 2,3-dichlorobenzoate (2,3-CBA) by SK-1. Duplicate cultures of SK-1 were used. The error bars represent a standard deviation. The control cultures contained 2,3-DCBP but lacked bacteria. The line with diamond points represents the control cultures. The line with square points represents the concentration of 2,3-DCBP in SK-1 cultures. The line with triangle points represents the generation of 2,3-dichlorobenzoate by SK-1 cultures.

Growth of bacterial strains SK-1 and SK-2 on 2,3-DCBP and 3,4-DCBP, respectively, as a sole carbon source was determined using direct counting and an acridine orange staining method. This method involves filtering 0.1 milliliters of culture through a 0.45 micron filter, staining the cells on the filter using a 0.01% acridine orange solution for 3 to 5 minutes, and counting cells on the filter using an epifluorescent microscope at a 1000' magnification. SK-1+ contained 2,3-dichlorobiphenyl; SK-2+ contained 3,4-dichlorobiphenyl. Control bottles in each case were identical to experimental bottles in that they were inoculated with the cultures but they lacked the appropriate congener. The initial concentration of PCBs was 500 ppm (w/v). The results of this experiment are indicated in FIG. 2. The cell numbers of the two isolates increased by 1.5 orders of magnitude in the presence of the DCBPs used as a growth substrate. The degradation of 2,3-DCBP by SK-1 and production of 2,3-dichlorobenzoate is depicted in FIG. 3. The degradation of 3,4-DCBP by SK-2 and production of 3,4-dichlorobenzoate is depicted in FIG. 4.

The concentrations of chlorobenzoates and dichlorobiphenyls were assessed after hexane extraction of bottles using gas chromatography analysis of the extracts with an electron capture detector. Chlorobenzoates were analyzed using standard columns after derivitization with pentafluorobenzyl bromide. Dichlorobiphenyls were analyzed using a DB-5 column (J&W Scientific, Fulsom, Calif.).

Figure 4:
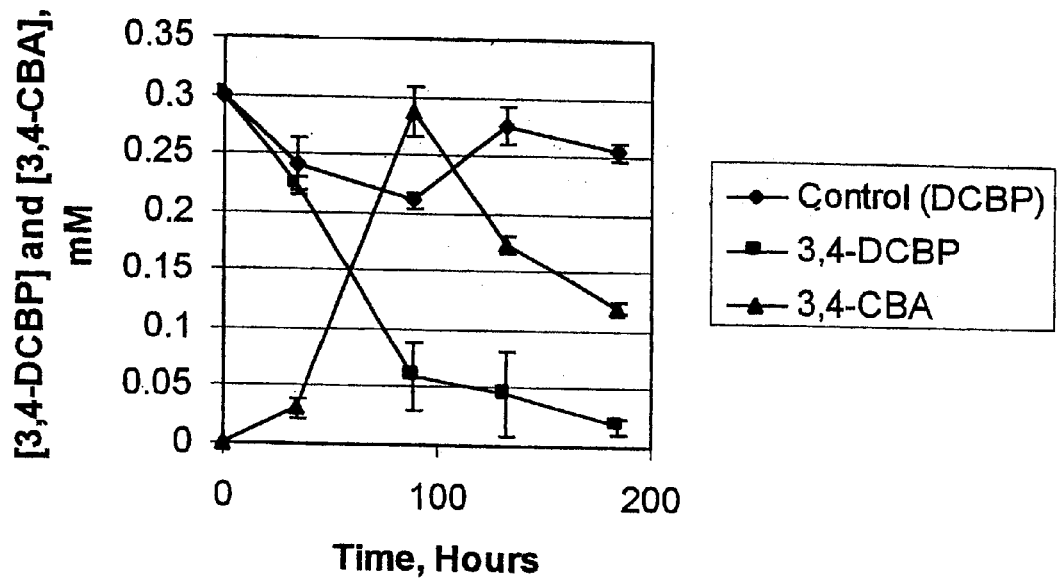
FIG. 4 is a graph depicting the degradation of 3,4-dichlorobiphenyl (3,4-DCBP) to 3,4-dichlorobenzoate (3,4-CBA) by SK-2. Duplicate cultures of SK-2 were used. The error bars represent a standard deviation. The control cultures contained 3,4-DCBP but lacked bacteria. The line with diamond points represent the control cultures. The line with square points represents the concentration of 3,4-DCBP in SK-2 cultures. The line with triangle points represents the generation of 3,4-dichlorobenzoate by SK-2 cultures.

The data shown in FIGS. 2, 3 and 4 illustrates the nearly complete disappearance of both 2,3-DCBP (0.38 mM initial concentration, FIG. 3) and 3,4-DCBP (0.3 mM initial concentration, FIG. 4) within 10 days of incubation. Duplicate bottles were used and error bars of the pictures represent a standard deviation. Controls contained DCBPs but lacked inoculum. DCBPs were supplied in the bottles using the non-biodegradable carrier heptamethylnonane (HMN). The data shown in FIG. 3 illustrates that the production of 2,3-chlorobenzoate (2,3-CBA) was almost stoichiometric. SK-2 also produced 3,4-CBA but the concentration of 3,4-CBA decreased after a maximum was reached at 90 hrs (FIG. 4).

Characterization of SK-3

Figure 5:
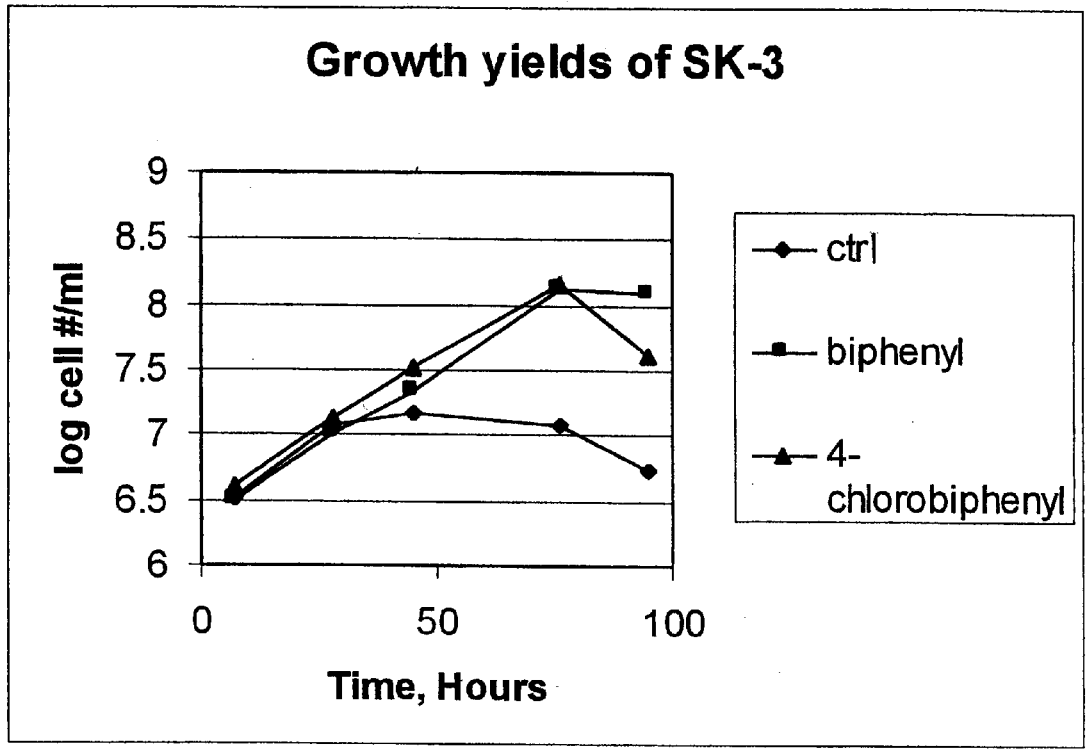
FIG. 5 is a graph depicting the cell growth of strain SK-3 on biphenyl and 4-chlorobiphenyl as sole carbon sources. Control cultures lacked a carbon source. The line with diamond points represent the growth of the control cultures. The line with square points represents the growth of SK-3 cultures on biphenyl and the line with triangle points represents the growth of SK-3 cultures on 4-chlorobiphenyl.

The growth of SK-3 on the monochlorobiphenyl 4-chlorobiphenyl and 4-chlorobenzoate as sole carbon sources was assessed. The results from this experiment are depicted in FIG. 5. SK-3 was able to grow rapidly on all of the three monochlorobiphenyls tested. The numbers of cells increased in the presence of the monochlorobiphenyl while the concentration of the monochlorobiphenyl decreased.

Figure 6:
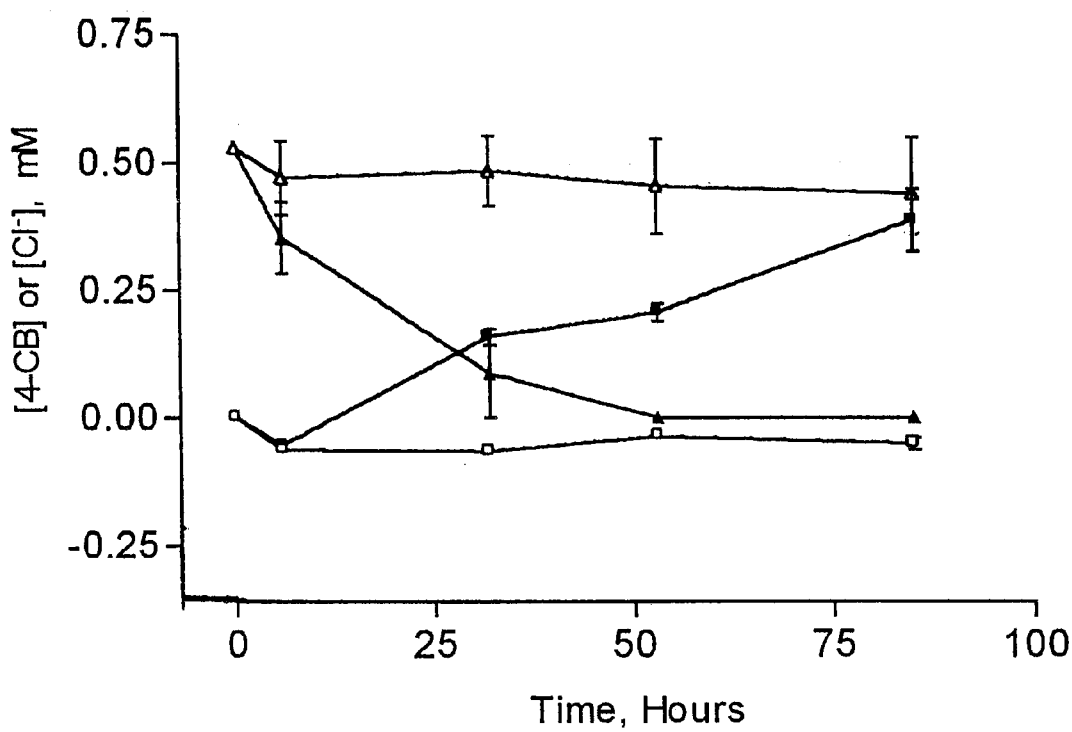
FIG. 6 is a graph depicting the degradation of 4-chlorobiphenyl (solid triangles) by SK-3 cultures. The controls are shown by the open triangles. The production of chloride by SK-3 cultures is shown by the closed squares and controls for chloride are shown by the open squares. Controls contained 4-chlorobiphenyl but lacked SK-3 cultures.

The growth of SK-3 on 4-chlorobiphenyl (4-CB) was compared with growth on its non-chlorinated form, biphenyl. The results were similar for cultures growing on biphenyl and 4-chlorobiphenyl. The biodegradation of 4-CB was assessed and the degradation resulted in the stoichiometric production of chloride. This indicates that the strain SK-3 is capable of growth on the chlorinated phenyl ring of 4-chlorobiphenyl. SK-3 is thus capable of growth on a mono-chlorobiphenyl as a sole carbon source. The results from this experiment are depicted in FIG. 6. The concentration of chloride ion was determined using ion chromatography on a standard Dionex ion chromatography column. The concentration of 4-CB was assessed after hexane extraction of bottles by analyzing the hexane extracts using gas chromatography on a DB-5 column (J&W Scientific, Fulsom, Calif.) and an electron capture detector.

In another experiment, the biodegradation of chlorobenzoates was assessed because chloride was released from the chlorobiphenyls during the experiment described above. Since chlorobenzoate accumulates as the product of PCB degradation in most cases, generation of chloride in the above experiment suggested the possible utilization of both rings of the chlorinated biphenyls.

Figure 7:
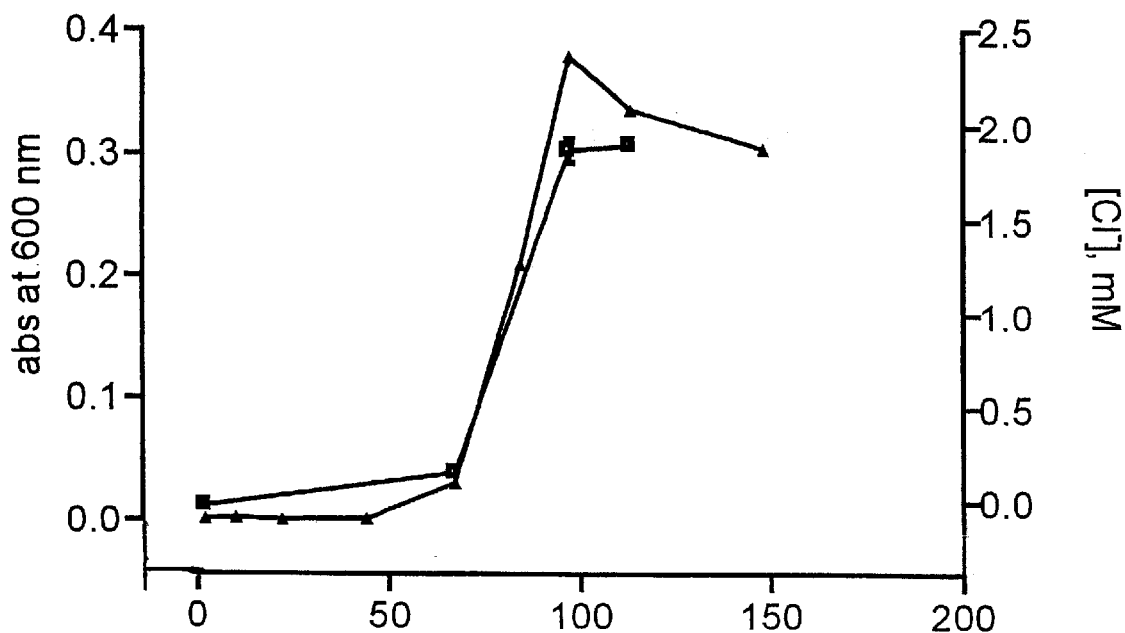
FIG. 7 is a graph depicting the growth curve of SK-3 on 4-chlorobenzoate as a sole carbon source and generation of chloride. The growth curve is indicated by the triangles and the chloride concentration is indicated by the squares.

The growth of SK-3 on chlorobenzoates was assessed. The cell density increased up to an optical density of 0.35 in the presence of 4-CBA. The analysis of chloride concentration as described herein also suggested that chloride was stoichiometrically released from 4-CBA. The results from this experiment are depicted in FIG. 7. The results from these experiments together suggest that 4-chlorobiphenyl is being mineralized (converted to carbon dioxide, water, and chloride) rather than being partially degraded to 4-chlorobenzoate. Thus, SK-3 is capable of more robust and efficient growth on PCBs than an organism capable of only partially degrading PCBs to a chlorobenzoate.

Figure 8:
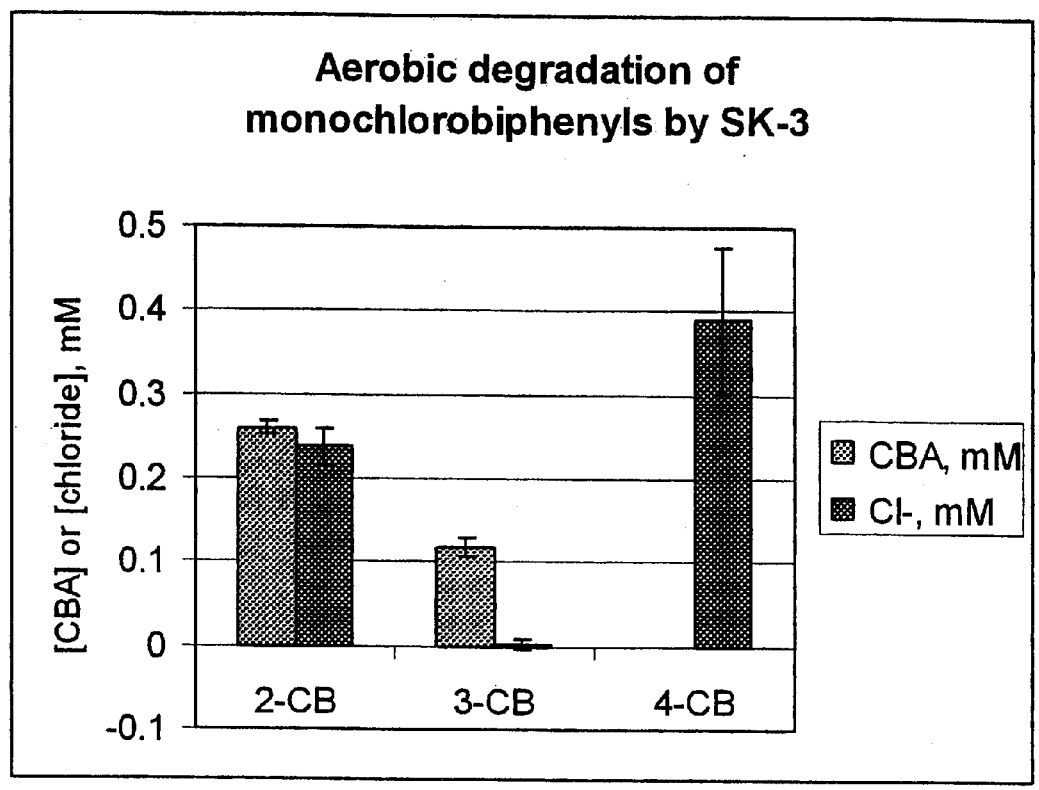
FIG. 8 is a graph depicting the degradation of monochlorobiphenyls (2-CB, 3-CB and 4-CB) by SK-3 with the resulting generation of chlorobenzoate (CBA) and chloride (Cl).

The degradation of three different monochlorobiphenyls, (2-CB, 3-CB, and 4-CB) by SK-3 was assessed at 23° C. under aerobic conditions on a shaker table. After incubation of SK-3 with the selected monochlorobiphenyl for 88 hours, the concentrations of chloride and the corresponding chlorobenzoic acids (CBA) was assessed as described herein. The results from this experiment are depicted in FIG. 8. SK-3 transformed 3-CB to 3-CBA without producing chloride. However, the degradation of 2-CB resulted in the partial release of chloride and production of 2-CBA. SK-3 did not generate 4-CBA during the growth on 4-CB. These results suggest that different monochlorobiphenyls are degraded using different metabolic pathways by the strain SK-3.

Figure 9:
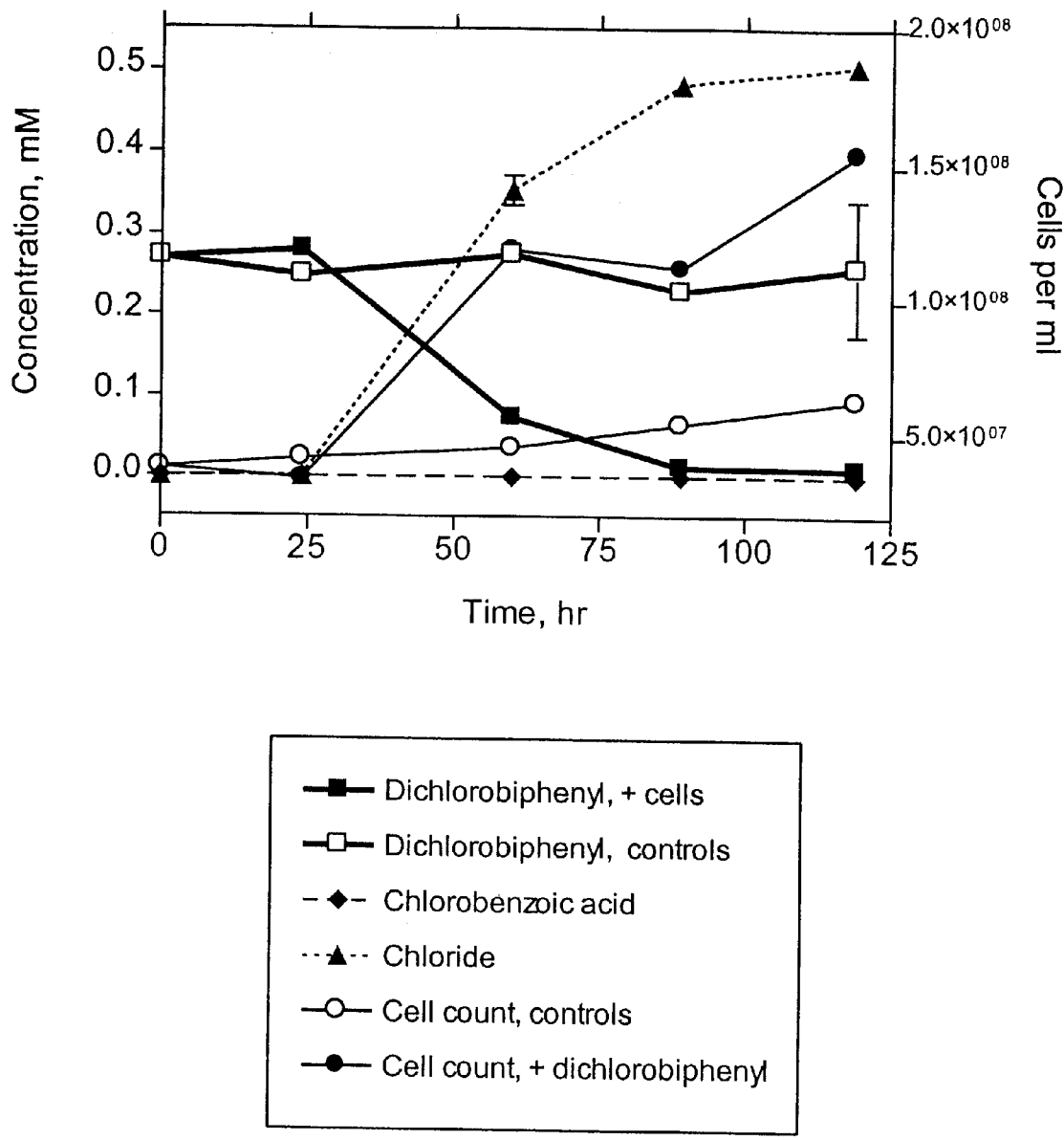
FIG. 9 is a graph depicting the growth curve of SK-3 on 2,4'-dichloro-biphenyl (2,4'-DCBP) as the sole carbon source, with the release of chloride ion. The concentration of 2,4'-DCBP is indicated by the open squares in the control (lacked a cell inoculum) and by the closed squares in the SK-3 cultures. The cell numbers are indicated by the open circles in the control cultures (contained heptamethylnonane carrier without 2,4'-DCBP) and by the closed circles in the SK-3 cultures which contained 2,4'-DCBP. The concentration of chloride ion is indicated by the closed triangles forming the dashed line and the concentration of chlorobenzoate is indicated by the closed diamonds forming the dashed line. Data was collected from two replicate samples and the error bars represent the standard deviations.

The growth of SK-3 on dichloro-biphenyls was also assessed. SK-3 was able to grow on 2,4'-DCBP (a dichlorinated biphenyl having a chlorine atom on both phenyl ring moieties) as the sole carbon source. The results of this experiment are depicted in FIG. 9. The doubling time of SK-3 when grown on 2,4'-DCBP at a concentration of 0.27 mM was approximately 43 hours. The production of chlorobenzoates (neither 2-CBA nor 4-CBA) was not detected during growth of SK-3 on 2,4'-DCBP. In contrast to the degradation of 2,4'-DCBP by SK-4 (described below), the extent of chloride production (0.49 mM) implied that both phenyl ring moieties of 2,4'-DCBP were dechlorinated and possibly also mineralized by SK-3.

Characterization of SK-4

The same methods for determining concentrations of analytes and for the incubation of the bacterial strain with growth substrate described herein for the previous analyses were used in the experiments to characterize SK-4. The concentration of SK-4 cells in the experiments was $1.5 \times 10^7$ cells per milliliter and the concentration of 2,2'-DCBP or 2,4'-DCBP was 100 milligrams per liter. The isolated bacterium SK-4 exhibited aerobic degradation of 2,2'-dichlorobiphenyl (2,2'-DCBP) and 2,4'-dichlorobiphenyl (2,4'-DCBP), and growth on each of 2,2'-DCBP and 2,4'-DCBP as a sole carbon source. This result is significant because these dichlorinated biphenyl congeners have a chlorine atom on both phenyl ring moieties in the ortho position. Ortho-substituted congeners are common degradation products of anaerobic reductive dechlorination of more highly chlorinated PCBs (PCBs comprising more than two chlorine atoms) by anaerobic bacteria. Thus, SK-4 may be used to enhance the bioremediation of highly chlorinated PCBs by anaerobic bacteria, whereby such enhanced bioremediation can result in the complete degradation and dechlorination of highly chlorinated PCBs.

Figure 10:
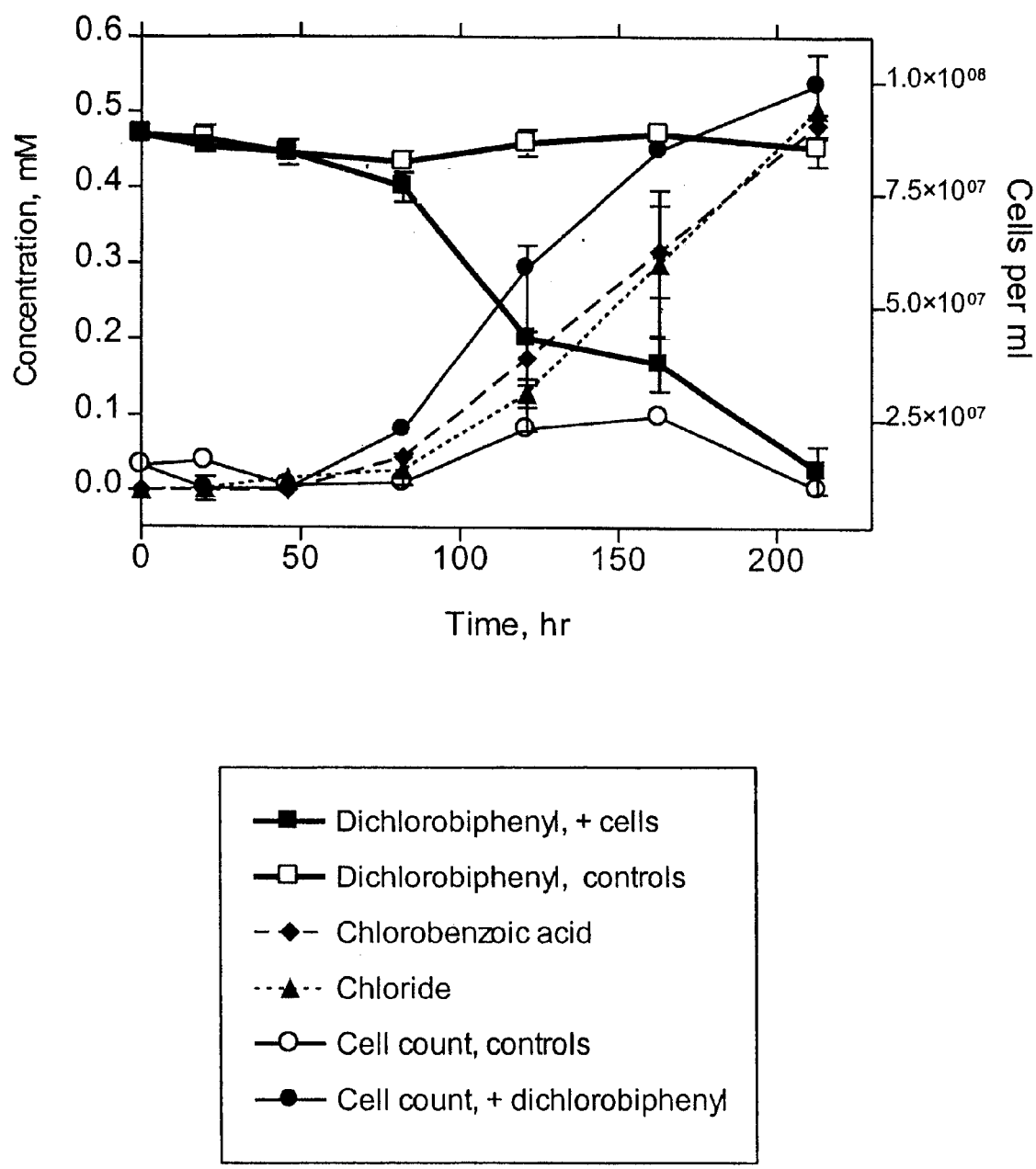
FIG. 10 is a graph depicting the growth curve of SK-4 on 2,2'-dichloro-biphenyl (2,2'-DCBP) as the sole carbon source, with the release of chloride ion and production of 2-chlorobenzoate. The concentration of 2,2'-DCBP is indicated by the open squares in the control (lacked a cell inoculum) and by the closed squares in the SK-4 cultures. The cell numbers are indicated by the open circles in the control cultures (contained heptamethylnonane carrier without 2,2'-DCBP) and by the closed circles in the SK-4 cultures which contained 2,2'-DCBP. The concentration of chloride ion is indicated by the closed triangles forming the dashed line and the concentration of 2-chlorobenzoate is indicated by the closed diamonds forming the dashed line. Data was collected from two replicate samples and the error bars represent the standard deviations.
Figure 11:
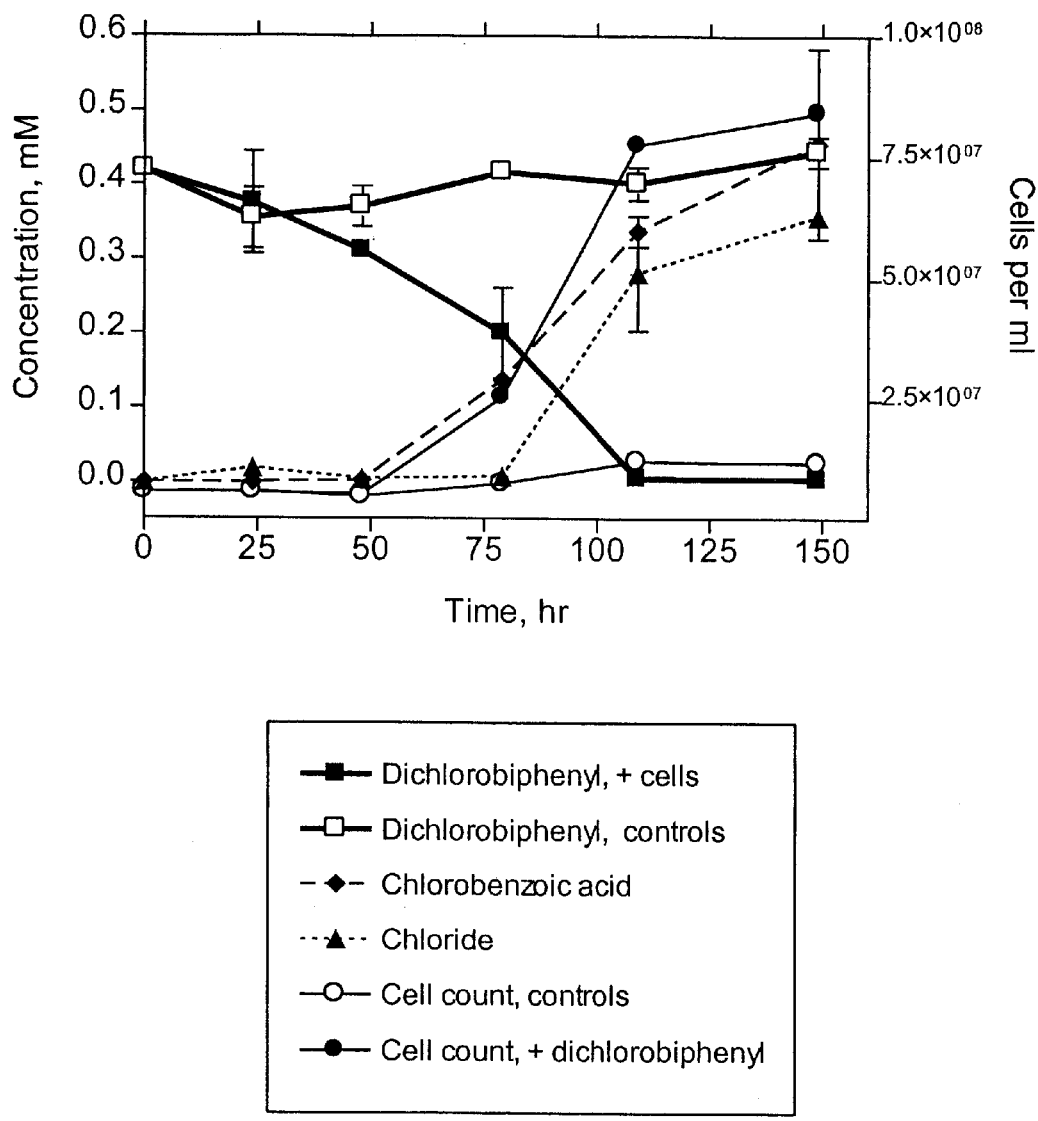
FIG. 11 is a graph depicting the growth curve of SK-4 on 2,4'-dichloro-biphenyl (2,4'-DCBP) as the sole carbon source, with release of chloride ion and production of 4-chlorobenzoate. The concentration of 2,4'-DCBP is indicated by the open squares in the control (lacked a cell inoculum) and by the closed squares in the SK-4 cultures. The cell numbers are indicated by the open circles in the control cultures (contained heptamethylnonane carrier without 2,4'-DCBP) and by the closed circles in the SK-4 cultures which contained 2,4'-DCBP. The concentration of chloride ion is indicated by the closed triangles forming the dashed line and the concentration of 4-chlorobenzoate is indicated by the closed diamonds forming the dashed line. Data was collected from two replicate samples and the error bars represent the standard deviations. Data was collected from two replicate samples and the error bars represent the standard deviations.

The results from these experiment are depicted in FIGS. 10 and 11. The data in FIG. 10 illustrate the growth curve of strain SK-4 on 2,2'-DCBP as the sole carbon source. 2,2'-DCBP was supplied at a concentration of 100 milligrams per liter dissolved in heptamethyl nonane (HMN), a non-biodegradable PCB solvent. Controls contained HMN but lacked 2,2'-DCBP. The data in FIG. 10 illustrate the degradation of 2,2'-DCBP by strain SK-4 and the resulting production of 2-chlorobenzoate (2-CBA). The 2,2'-DCBP was completely transformed into 2-CBA with accompanying stoichiometric release of chloride, as depicted in FIG. 10.

In addition to 2,2'-DCBP, SK-4 also exhibited the ability to grow on 2,4'-DCBP, another ortho-chlorinated dichlorobiphenyl, as depicted in FIG. 11. As illustrated in FIG. 11, SK-4 exhibited the ability to grow rapidly on 2,4'-DCBP at a concentration of 0.42 mM, with an approximate doubling time of 17 hours. As in the degradation of 2,2'-DCBP, growth on 2,4'-DCBP resulted in the stoichiometric accumulation of a chlorobenzoate and the production of chloride. The chlorobenzoate produced was identified as 4-CBA, suggesting that SK-4 utilized only the ortho-chlorinated phenyl rings of 2,2'-DCBP or 2,4'-DCBP.

TABLE 1

Identification of isolated PCB-degrading bacteria

| Methods | SK-1 | SK-2 | SK-3 | SK-4 |
|---|---|---|---|---|
| API 20E[1] | P. putida<br>P. fluorescens | P. fluorescens<br>Other Pseudo. spp. | P. putida<br>P. fluorescens | Pseudomonas sp.<br>Alcaligenes spp. |
| Microbial ID | Burkholderia solanacearum<br>Burkholderia pikettii | Alcaligenes piechaudii<br>Alcaligenes xylosoxydans | Burkholderia solanacearum<br>Burkholderia pikettii | Alcaligenes eutrophus |

TABLE 2

Growth substrate tests for dichlorobiphenyl (DCBP)- and trichlorobiphenyl (TCBP)-degrading bacteria

|  | SK-1 | SK-2 | SK-3 | SK-4 |
|---|---|---|---|---|
| Benzoate | Yes | Yes | Yes | Yes |
| Biphenyl | Yes | Yes | Yes | Yes |
| 2-chlorobiphenyl | Yes | Yes | Yes | Yes |
| 3-chlorobiphenyl | Yes | Yes | Yes | Yes |
| 4-chlorobiphenyl | Yes | Yes | Yes | Yes |
| 2,3-DCBP | Yes | No | No | No |
| 3,4-DCBP | No | Yes | No | No |
| 2,2'-DCBP | No | No | No | Yes |
| 3,5-DCBP | No | No | No | No |
| 3,3'-DCBP | N/D | N/D | No | No |
| 4,4'-DCBP | N/D | N/D | No | No |
| 2,4'-DCBP | Yes | Unlikely | Yes | Yes |
| 2,5-DCBP | Likely | No | No | No |
| 2,3'-DCBP | No | No | No | No |
| 2,2',5-TCBP | N/D | N/D | N/D | No |
| 2,2',3-TCBP | No | No | No | No |
| 2',3,4-TCBP | No | No | No | No |
| Chloroacetate | Yes | No | Yes | Yes |
| Phenol | Yes | No | Yes | Yes |
| Naphthalene | No | No | No | No |
| 2-chlorobenzoate | No | No | No | No |
| 3-chlorobenzoate | No | No | No | No |
| 4-chlorobenzoate | No | No | Yes | No |
| 2,3-dichlorobenzoate | No | No | No | No |
| 3,4-dichlorobenzoate | N/D | N/D | No | No |
| 2,3,4-trichlorobenzoate | No | No | No | N/D |

N/D - Not determined.

(All tests were conducted in a liquid medium. The initial concentration of the organic substrate was 100 parts per million, except chlorobenzoate, which was 2–3 millimolar).

SUMMARY OF RESULTS

The results presented in this Example indicate that the isolated bacterium which were isolated and characterized herein were capable of growth on polychlorinated biphenyls (PCBs) as a sole carbon source. In particular, strains SK-1, SK-2, SK-3 and SK-4 exhibited growth on dichlorobiphenyls as a sole carbon source. Strains SK-3 and SK-4 exhibited growth on a dichlorobiphenyl having a chlorine atom on both phenyl ring moieties.

The isolation and characterization of these isolated bacteria was significant because these were the first isolated naturally occurring bacteria having the ability to grow on a polychlorinated biphenyl as a sole carbon source. Strains SK-3 and SK-4 exhibited the further advantageous ability to grow on a dichlorobiphenyl congener having a chlorine atom on each phenyl ring, as opposed to both chlorine atoms on the same phenyl ring. Only one other organism, which is a recombinant organism has been reported to have the ability to grow on a PCB congener having a chlorine atom on both phenyl rings (McCullar et al., 1994, Applied and Environ. Microbiol. 60:3833–3839).

The isolated bacteria of the invention thus have utility in methods for the bioremediation of PCB contaminated wastes such as sludges, soils, sediments and wastewaters for two main reasons. First, because the strains are naturally isolated, there is less cost and effort involved in obtaining the strains than in genetically engineering a recombinant microorganism.

The second major beneficial feature of the isolated bacteria of the invention is the fact that they are capable of growth on dichlorobiphenyls without any other added carbon source. This is important because, until now, naturally obtained microorganisms have required the addition of a second carbon substrate, such as biphenyl or napthalene, to carry out the cometabolism of PCBs along with the cosubstrate. Thus, the strains of the invention can be used in bioremediation without requiring the addition of chemicals to waste, such as biphenyl and napthalene, which are themselves toxic to living systems.

Thus, the isolated new strains of the invention represent a valuable tool for use in PCB bioremediation. The strains can be used effectively as individual strains, as a combination of several strains of the invention, in combination with other microorganisms, or in combination with other treatment methods such as enzymes or chemicals capable of degrading PCBs or partially degrading PCBs.

EXAMPLE 2

Biodegradation of a Commercial PCB Mixture by SK-1, SK-2, SK-3 and SK-4

In addition to testing the ability to use a single PCB congener as a sole carbon source (as described in Example 1), several strains of the isolated bacteria of the invention (SK-1, SK-2, SK-3 and SK-4) were tested for the ability to degrade low chlorinated PCB congeners (dichlorobiphenyls and trichlorobiphenyls) of a commercial PCB mixture in the absence of biphenyl or any other cometabolic substrate as a carbon source.

The ability of SK-1, SK-2, SK-3 and SK-4 to degrade Aroclor® 1242 was assessed using cells which were grown on benzoate and then washed. Briefly, the cells were washed by centrifuging the cells, decanting the supernatant, resuspending the cells in fresh medium, then pelleting the cells using centrifugation again and decanting the supernatant to remove residual benzoate and other carbon sources. Aroclor® 1242 was the sole carbon source provided to the cells.

Figure 12A:
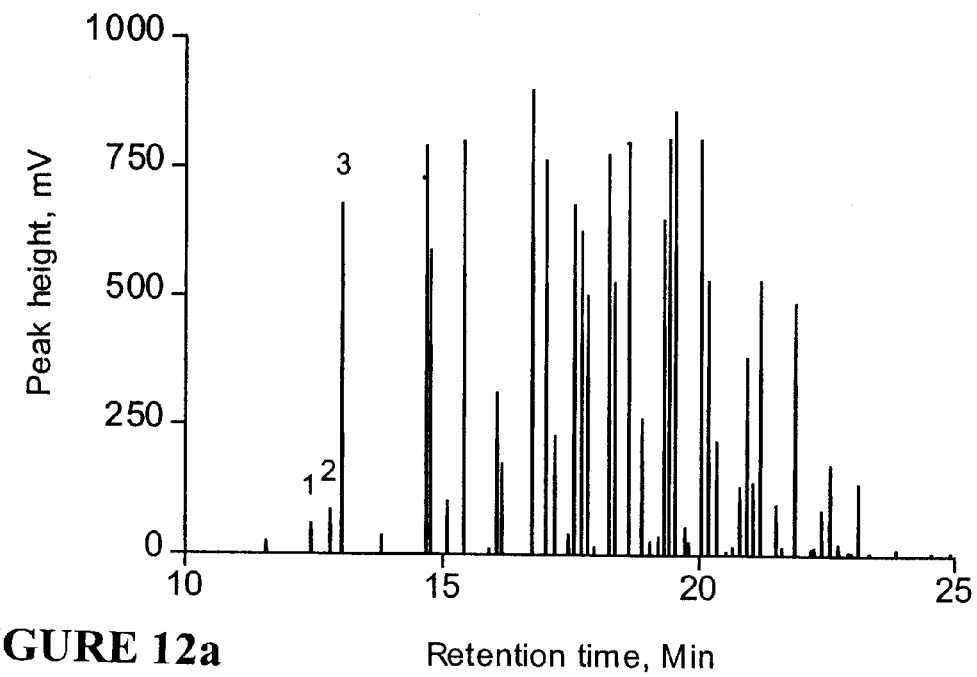
FIGS. 12A and 12B, is a pair of images of chromatograms from gas chromatography analysis of a control sample of Aroclor® 1242, and a sample of Aroclor® 1242 after incubation with benzoate-grown SK-3, respectively. The dichlorobiphenyls of Aroclor® 1242 indicated as peaks 1, 2, and 3 were degraded during the incubation with benzoate-grown SK-3.
Figure 12B:
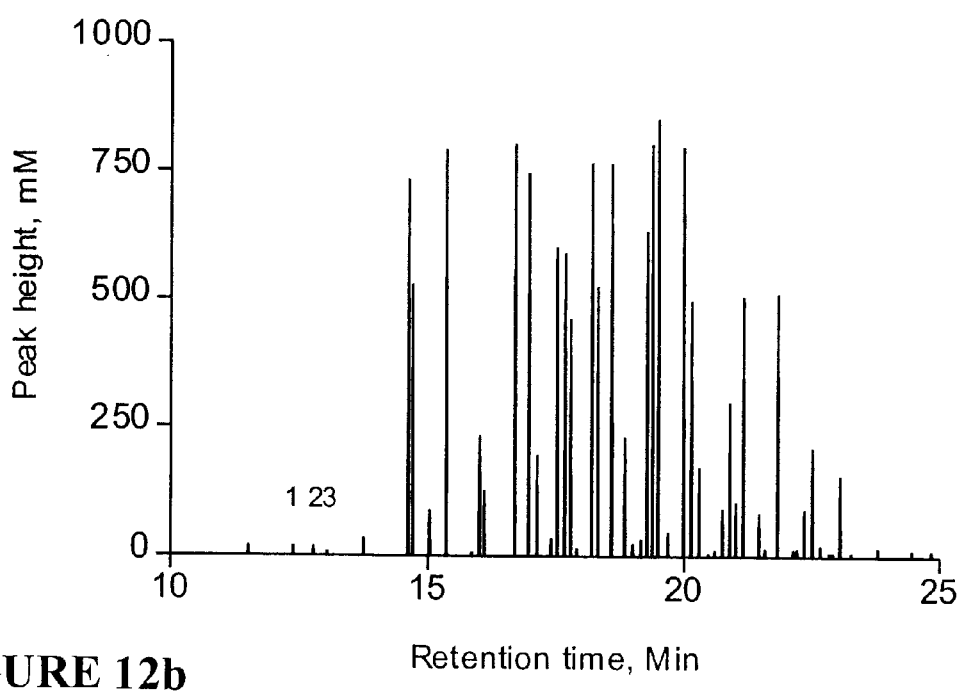

The degradation of Aroclor® 1242 by SK-3 was monitored using gas is chromatography analysis and the results are depicted in FIG. 12. After 12 days incubation with SK-3, three lightly chlorinated biphenyls of Aroclor® 1242 were found to be degraded. The individual congeners degraded were identified by comparing the retention times of the peaks which were significantly diminished in height after incubation with SK-3 with the retention times of corresponding peaks in the control chromatogram obtained from a sample of Aroclor® 1242 which was not incubated with SK-3 cells (FIG. 12A). The degraded PCB congeners were identified as follows: Peak #1 was 2,5-DCBP or 2,4-DCBP; Peak #2 was 2,3'-DCBP; and Peak #3 was 2,4'-DCBP. No significant degradation of any PCB congener containing three or more chlorine atoms was observed.

Figure 13A:
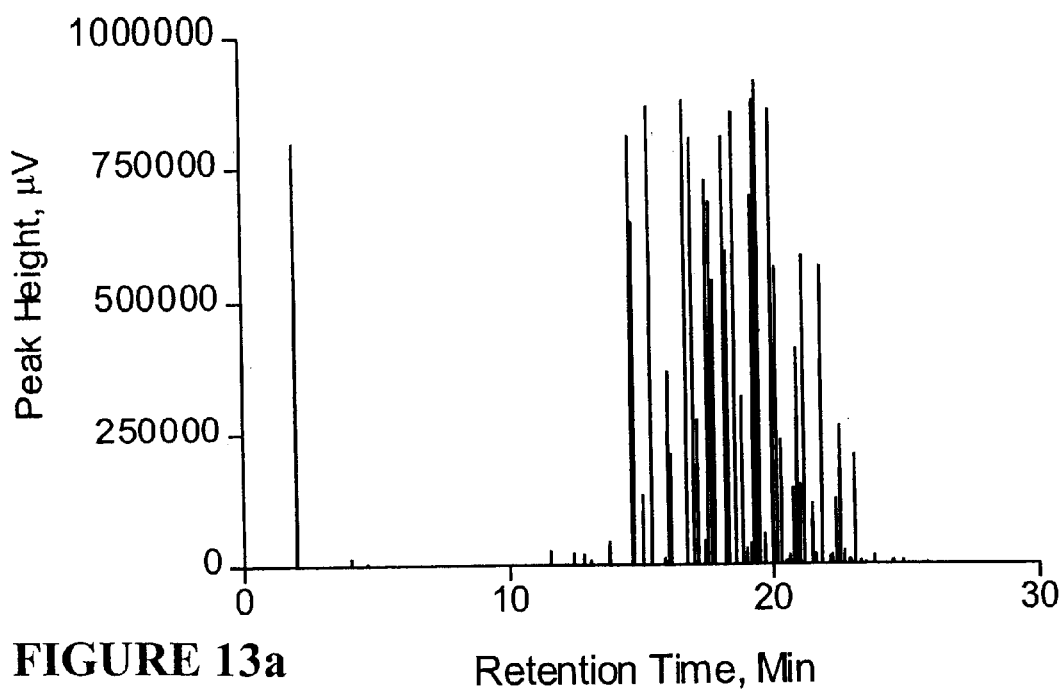
FIGS. 13A and 13B, is a pair of images of chromatograms from gas chromatography analysis of a sample of Aroclor® 1242 after incubation for 12 days with benzoate-grown SK-1, and a sample of Aroclor® 1242 after incubation for 12 days with benzoate-grown SK-2, respectively. The chromatogram from gas chromatography analysis of a control sample of Aroclor® 1242 is depicted in FIG. 12A.
Figure 13B:
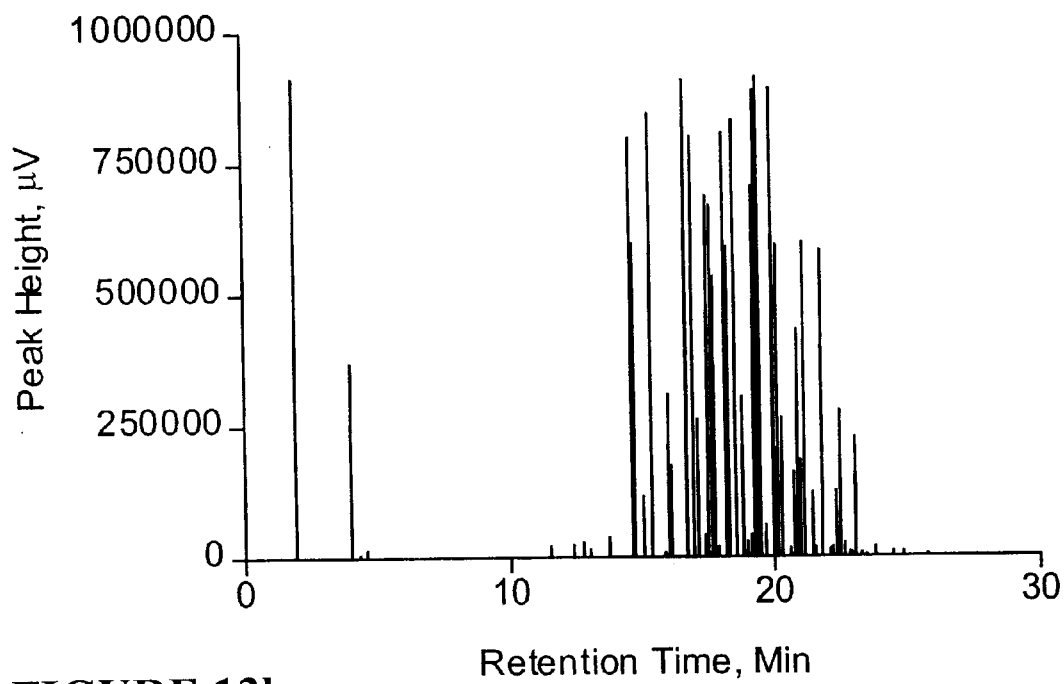
Figure 14:
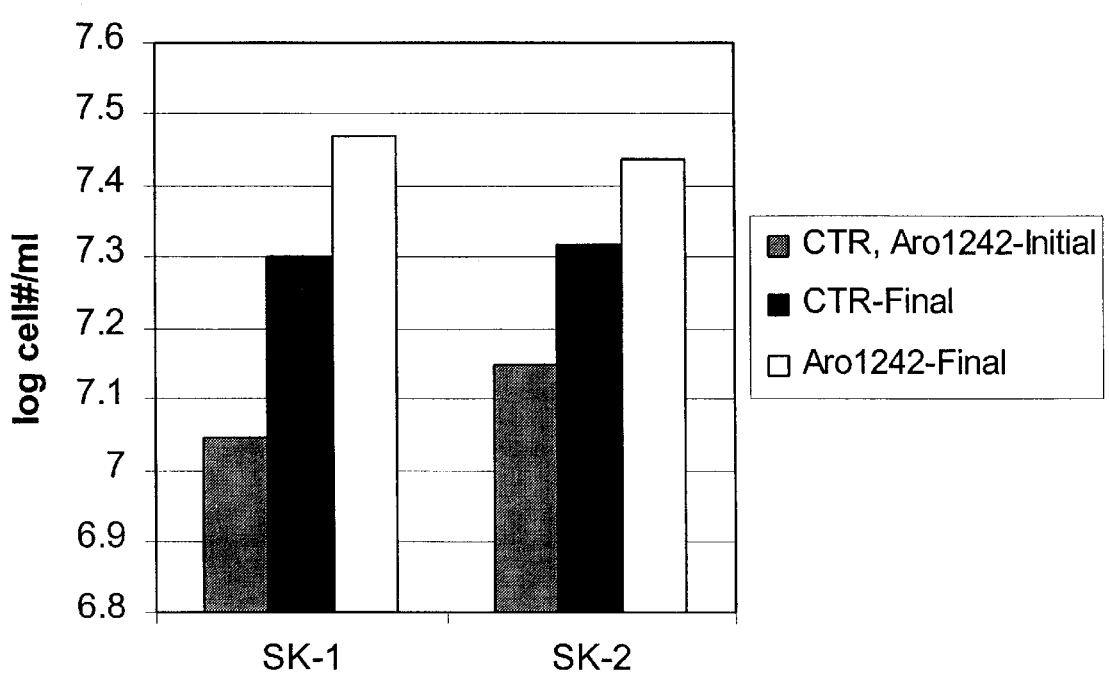
FIG. 14 is a graph depicting initial and final cell numbers of SK-1 and SK-2 before and after 12 days of incubation with Aroclor® 1242 at a concentration of 250 parts per million. The control cultures (CTR) were not incubated with Aroclor® 1242. Cell numbers were counted using the acridine orange direct counting method descibed herein.

SK-1 and SK-2 exhibited very similar abilities to degrade low-chlorinated PCBs in Aroclor® 1242. The chromatograms obtained from Aroclor® 1242 before and after incubation with either SK-1 or SK-2 indicated that several less chlorinated PCB congeners were depleted during the incubation, as indicated in FIG. 13. During the incubation period, a small increase in both SK-1 and SK-2 cell numbers was observed, as depicted in FIG. 14, indicating growth on Aroclor® 1242.

Figure 15A:
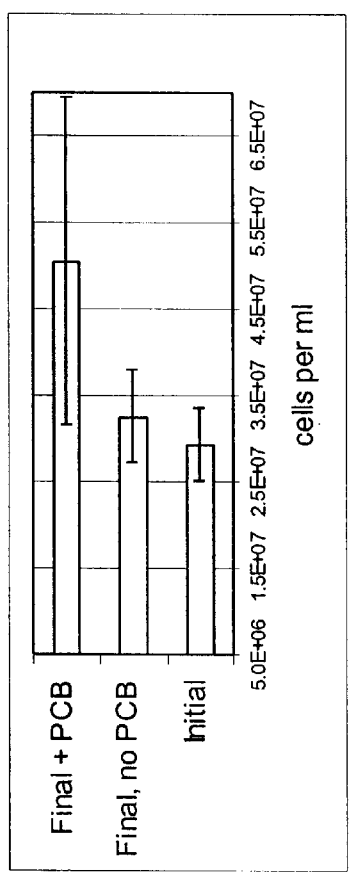
FIGS. 15A and 15B, is a pair of images illustrating the results of incubation of SK-4 with Aroclor® 1242 for 12 days.
Figure 15B:
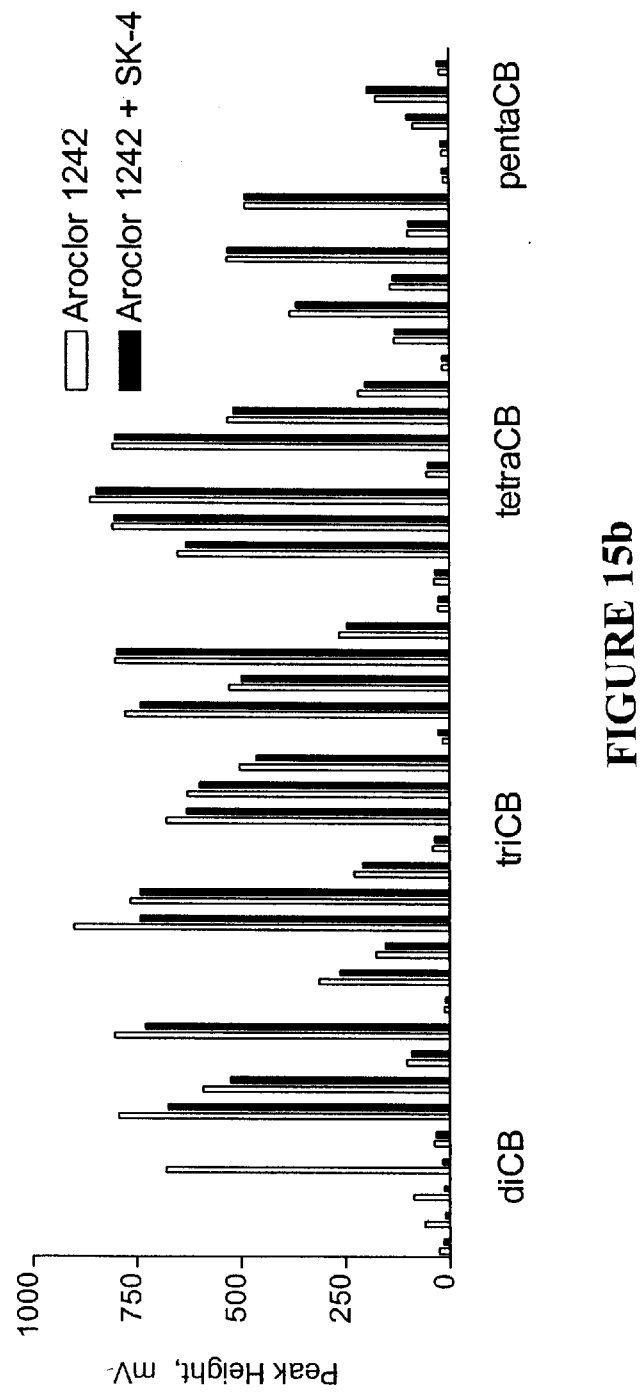

Strain SK-4 exhibited the ability to nearly completely degrade all of the dichlorobiphenyl congeners in Aroclor® 1242 without the need for a cometabolic substrate or previous growth on biphenyl, as depicted in FIG. 15. A minor decrease in several trichlorobiphenyl congeners (TCBPs) was also observed, as was a minor increase in SK-4 cell number (FIG. 15). However, it is unclear whether the degradation of TCBPs supported growth or whether their degradation was merely cometabolic during growth of SK-4 on 2,2'-DCBP or 2,4'-DCBP.

In view of the demonstrated ability of SK-1, SK-2, SK-3 and SK-4 to tolerate a relatively high PCB concentration while degrading several multichlorinated congeners, these isolated bacteria of the invention are valuable for in situ biodegradation of PCBs and PCB bioremediation methods which are free from the requirement of any toxic cosubstrates.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

DEPOSIT

Under the terms of the Budapest Treaty on the International Recognition of the Deposit of Microorganisms for the Purpose of Patent Procedure, deposit of four bacterial strains, SK-1, SK-2, SK-3, and SK-4, is being made with the Agricultural Research Service Culture Collection (NRRL) of Peoria, Ill., USA, where the deposits are given NRRL Accession Numbers B30543, B30544, B30545 and B30546.

Applicant's assignee, Indiana University, Advanced Research and Technology Institute, represents that the NRRL is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. § 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicant's assignee acknowledges its duty to replace the deposit should the depository be unable to furnish a sample when requested due to the condition of the deposit.

What is claimed is:

1. An isolated bacterium that utilizes as a sole carbon source a polychlorinated biphenyl (PCB), wherein said polychlorinated biphenyl is 2,3-dichloro-biphenyl and said bacterium is strain SK-1 (NRRL Accession No. B30543).

2. An isolated bacterium that utilizes as a sole carbon source a polychlorinated biphenyl, wherein said polychlorinated biphenyl is 3,4-dichloro-biphenyl and said bacterium is strain SK-2 (NRRL Accession No. B30544).

3. An isolated bacterium that utilizes as a sole carbon source a polychlorinated biphenyl, wherein said polychlorinated biphenyl is 2,2'-dichloro-biphenyl and said bacterium is strain SK-4 (NRRL Accession No. B30546).

4. An isolated bacterium that utilizes as a sole carbon source a polychlorinated biphenyl, wherein said polychlorinated biphenyl is 2,4'-dichloro-biphenyl and said bacterium is strain SK-3 (NRRL Accession No. B30545).

5. An isolated bacterium that utilizes as a sole carbon source a polychlorinated biphenyl, wherein said polychlorinated biphenyl is 2,4'-dichloro-biphenyl and said bacterium is strain SK-4 (NRRL Accession No. B30546).

6. A method for the bioremediation of a PCB-contaminated environment comprising 2,3-dichloro-biphenyl, said method comprising:
   a) adding the isolated bacterium of claim 1 to said PCB-contaminated environment, wherein said bacterium is capable of utilizing as a sole carbon source 2,3-dichloro-biphenyl, and
   b) incubating said bacterium in said environment for a period of time sufficient to permit degradation of 2,3-dichloro-biphenyl in said environment, thereby bioremediating said environment.

7. A method for enhancing the bioremediation of a PCB-contaminated environment consisting of 2,3-dichloro-biphenyl and at least one agent useful in the bioremediation of polychlorobiphenyls, wherein said agent is selected from the group consisting of a PCB-degrading microorganism and a PCB-degrading chemical compound, said method comprising:
   a) adding the isolated bacterium of claim 1 to said PCB-contaminated environment, wherein said bacterium is capable of utilizing as a sole carbon source 2,3dichloro-biphenyl, and
   b) incubating said bacterium in said environment for a period of time sufficient to permit degradation of 2,3-dichloro-biphenyl in said environment, thereby enhancing the bioremediation of said environment.

8. A method for the bioremediation of a PCB-contaminated environment comprising 2,3-dichloro-biphenyl, said method comprising:
   a) adding the isolated bacterium of claim 1 to said PCB-contaminated environment, wherein said bacterium is capable of utilizing as a sole carbon source 2,3-dichloro-biphenyl;
   b) adding a cosubstrate selected from the group consisting of biphenyl and naphthalene to said PCB-contaminated environment whereby cometabolism of said cosubstrate and 2,3-dichloro-biphenyl may occur, and
   c) incubating said bacterium in said environment for a period of time sufficient to permit degradation of 2,3-dichloro-biphenyl in said environment, thereby bioremediating said environment.

9. A method for the bioremediation of a PCB-contaminated environment comprising 2,3-dichloro-biphenyl, said method comprising:
   a) adding an isolated first bacterium of claim 1 to said PCB-contaminated environment, wherein said bacterium is capable of utilizing as a sole carbon source 2,3-dichloro-biphenyl;
   b) adding an isolated second bacterium to said PCB-contaminated environment, wherein said second isolated bacterium is capable of utilizing a chlorobenzoate as a sole carbon source, and
   c) incubating said isolated first and second bacteria in said environment for a period of time sufficient to permit degradation of 2,3-dichloro-biphenyl and a chlorobenzoate in said environment, thereby bioremediating said environment.

10. A method for the bioremediation of a PCB-contaminated environment comprising 3,4-dichloro-biphenyl, said method comprising:
    a) adding the isolated bacterium of claim 2 to said PCB-contaminated environment, wherein said bacterium is capable of utilizing as a sole carbon source 3,4-dichloro-biphenyl, and
    b) incubating said bacterium in said environment for a period of time sufficient to permit degradation of 3,4-dichloro-biphenyl in said environment, thereby bioremediating said environment.

11. A method for enhancing the bioremediation of a PCB-contaminated environment consisting of 3,4-dichloro-biphenyl and at least one agent useful in the bioremediation of polychlorobiphenyls, wherein said agent is selected from the group consisting of a PCB-degrading microorganism and a PCB-degrading chemical compound, said method comprising:
    a) adding the isolated bacterium of claim 2 to said PCB-contaminated environment, wherein said bacterium is capable of utilizing as a sole carbon source 3,4-dichloro-biphenyl, and
    b) incubating said bacterium in said environment for a period of time sufficient to permit degradation of 3,4-dichloro-biphenyl in said environment, thereby enhancing the bioremediation of said environment.

12. A method for the bioremediation of a PCB-contaminated environment comprising 3,4-dichloro-biphenyl, said method comprising:
    a) adding the isolated bacterium of claim 2 to said PCB-contaminated environment, wherein said bacterium is capable of utilizing as a sole carbon source 3,4-dichloro-biphenyl;
    b) adding a cosubstrate selected from the group consisting of biphenyl and naphthalene to said PCB-contaminated environment whereby cometabolism of said cosubstrate and 3,4-dichloro-biphenyl may occur, and c) incubating said bacterium in said environment for a period of time sufficient to permit degradation of 3,4-dichloro-biphenyl in said environment, thereby bioremediating said environment.

13. A method for the bioremediation of a PCB-contaminated environment comprising 3,4-dichloro-biphenyl, said method comprising:
   a) adding an isolated first bacterium of claim 2 to said PCB-contaminated environment, wherein said bacterium is capable of utilizing as a sole carbon source 3,4-dichloro-biphenyl;
   b) adding an isolated second bacterium to said PCB-contaminated environment, wherein said second isolated bacterium is capable of utilizing a chlorobenzoate as a sole carbon source, and
   c) incubating said isolated first and second bacteria in said environment for a period of time sufficient to permit degradation of 3,4-dichloro-biphenyl and a chlorobenzoate in said environment, thereby bioremediating said environment.

14. A method for the bioremediation of a PCB-contaminated environment comprising 2,2'-dichloro-biphenyl, said method comprising:
   a) adding the isolated bacterium of claim 3 to said PCB-contaminated environment, wherein said bacterium is capable of utilizing as a sole carbon source 2,2'-dichloro-biphenyl, and
   b) incubating said bacterium in said environment for a period of time sufficient to permit degradation of 2,2'-dichloro-biphenyl in said environment, thereby bioremediating said environment.

15. A method for enhancing the bioremediation of a PCB-contaminated environment consisting of 2,2'-dichloro-biphenyl and at least one agent useful in the bioremediation of polychlorobiphenyls, wherein said agent is selected from the group consisting of a PCB-degrading microorganism and a PCB-degrading chemical compound, said method comprising:
   a) adding the isolated bacterium of claim 3 to said PCB-contaminated environment, wherein said bacterium is capable of utilizing as a sole carbon source 2,2'-dichloro-biphenyl, and
   b) incubating said bacterium in said environment for a period of time sufficient to permit degradation of 2,2'-dichloro-biphenyl in said environment, thereby enhancing the bioremediation of said environment.

16. A method for the bioremediation of a PCB-contaminated environment comprising 2,2'-dichloro-biphenyl, said method comprising:
   a) adding the isolated bacterium of claim 3 to said PCB-contaminated environment, wherein said bacterium is capable of utilizing as a sole carbon source 2,2'-dichloro-biphenyl;
   b) adding a cosubstrate selected from the group consisting of biphenyl and naphthalene to said PCB-contaminated environment whereby cometabolism of said cosubstrate and 2,2'-dichloro-biphenyl may occur, and
   c) incubating said bacterium in said environment for a period of time sufficient to permit degradation of 2,2'-dichloro-biphenyl in said environment, thereby bioremediating said environment.

17. A method for the bioremediation of a PCB-contaminated environment comprising 2,2'-dichloro-biphenyl, said method comprising:
   a) adding an isolated first bacterium of claim 3 to said PCB-contaminated environment, wherein said bacterium is capable of utilizing as a sole carbon source 2,2'-dichloro-biphenyl;.
   b) adding an isolated second bacterium to said PCB-contaminated environment, wherein said second isolated bacterium is capable of utilizing a chlorobenzoate as a sole carbon source, and
   c) incubating said isolated first and second bacteria in said environment for a period of time sufficient to permit degradation of 2,2'-dichloro-biphenyl and a chlorobenzoate in said environment, thereby bioremediating said environment.

18. A method for the bioremediation of a PCB-contaminated environment comprising 2,4'-dichloro-biphenyl, said method comprising:
   a) adding the isolated bacterium of claim 4 to said PCB-contaminated environment, wherein said bacterium is capable of utilizing as a sole carbon source 2,4'-dichloro-biphenyl, and
   b) incubating said bacterium in said environment for a period of time sufficient to permit degradation of 2,4'-dichloro-biphenyl in said environment, thereby bioremediating said environment.

19. A method for enhancing the bioremediation of a PCB-contaminated environment consisting of 2,4'-dichloro-biphenyl and at least one agent useful in the bioremediation of polychlorobiphenyls, wherein said agent is selected from the group consisting of a PCB-degrading microorganism and a PCB-degrading chemical compound, said method comprising:
   a) adding the isolated bacterium of claim 4 to said PCB-contaminated environment, wherein said bacterium is capable of utilizing as a sole carbon source 2,4'-dichloro-biphenyl, and
   b) incubating said bacterium in said environment for a period of time sufficient to permit degradation of 2,4'-dichloro-biphenyl in said environment, thereby enhancing the bioremediation of said environment.

20. A method for the bioremediation of a PCB-contaminated environment comprising 2,4'-dichloro-biphenyl, said method comprising:
   a) adding the isolated bacterium of claim 4 to said PCB-contaminated environment, wherein said bacterium is capable of utilizing as a sole carbon source 2,4'-dichloro-biphenyl;
   b) adding a cosubstrate selected from the group consisting of biphenyl and naphthalene to said PCB-contaminated environment whereby cometabolism of said cosubstrate and 2,4'-dichloro-biphenyl may occur, and
   c) incubating said bacterium in said environment for a period of time sufficient to permit degradation of 2,4'-dichloro-biphenyl in said environment, thereby bioremediating said environment.

21. A method for the bioremediation of a PCB-contaminated environment comprising 2,4'-dichloro-biphenyl, said method comprising:
   a) adding an isolated first bacterium of claim 4 to said PCB-contaminated environment, wherein said bacterium is capable of utilizing as a sole carbon source 2,4'-dichloro-biphenyl;
   b) adding an isolated second bacterium to said PCB-contaminated environment, wherein said second isolated bacterium is capable of utilizing a chlorobenzoate as a sole carbon source, and
   c) incubating said isolated first and second bacteria in said environment for a period of time sufficient to permit degradation of 2,4'-dichloro-biphenyl and a chlorobenzoate in said environment, thereby bioremediating said environment.

22. A method for the bioremediation of a PCB-contaminated environment comprising 2,4'-dichloro-biphenyl, said method comprising:
   a) adding the isolated bacterium of claim 5 to said PCB-contaminated environment, wherein said bacterium is capable of utilizing as a sole carbon source 2,4'-dichloro-biphenyl, and
   b) incubating said bacterium in said environment for a period of time sufficient to permit degradation of 2,4'-dichloro-biphenyl in said environment, thereby bioremediating said environment.

23. A method for enhancing the bioremediation of a PCB-contaminated environment consisting of 2,4'-dichloro-biphenyl and at least one agent useful in the bioremediation of polychlorobiphenyls, wherein said agent is selected from the group consisting of a PCB-degrading microorganism and a PCB-degrading chemical compound, said method comprising:
   a) adding the isolated bacterium of claim 5 to said PCB-contaminated environment, wherein said bacterium is capable of utilizing as a sole carbon source 2,4'-dichloro-biphenyl, and
   b) incubating said bacterium in said environment for a period of time sufficient to permit degradation of 2,4'-dichloro-biphenyl in said environment, thereby enhancing the bioremediation of said environment.

24. A method for the bioremediation of a PCB-contaminated environment comprising 2,4'-dichloro-biphenyl, said method comprising:
   a) adding the isolated bacterium of claim 5 to said PCB-contaminated environment, wherein said bacterium is capable of utilizing as a sole carbon source 2,4'-dichloro-biphenyl;
   b) adding a cosubstrate selected from the group consisting of biphenyl and naphthalene to said PCB-contaminated environment whereby cometabolism of said cosubstrate and 2,4'-dichloro-biphenyl may occur, and
   c) incubating said bacterium in said environment for a period of time sufficient to permit degradation of 2,4'-dichloro-biphenyl in said environment, thereby bioremediating said environment.

25. A method for the bioremediation of a PCB-contaminated environment comprising 2,4'-dichloro-biphenyl, said method comprising:
   a) adding an isolated first bacterium of claim 5 to said PCB-contaminated environment, wherein said bacterium is capable of utilizing as a sole carbon source 2,4'-dichloro-biphenyl;
   b) adding an isolated second bacterium to said PCB-contaminated environment, wherein said second isolated bacterium is capable of utilizing a chlorobenzoate as a sole carbon source, and
   c) incubating said isolated first and second bacteria in said environment for a period of time sufficient to permit degradation of 2,4'-dichloro-biphenyl and a chlorobenzoate in said environment, thereby bioremediating said environment.

* * * * *